United States Patent
Kwon et al.

(10) Patent No.: US 12,420,086 B2
(45) Date of Patent: Sep. 23, 2025

(54) METHOD OF MANUFACTURING NERVE ELECTRODE

(71) Applicant: UNIVERSITY-INDUSTRY COOPERATION GROUP OF KYUNG HEE UNIVERSITY, Yongin-si (KR)

(72) Inventors: Il Keun Kwon, Seoul (KR); Dong Nyoung Heo, Seoul (KR); Dong Hyun Lee, Seoul (KR); Sang Jin Lee, Anyang-si (KR); Min Heo, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 1114 days.

(21) Appl. No.: 16/471,354

(22) PCT Filed: Mar. 30, 2017

(86) PCT No.: PCT/KR2017/003465
§ 371 (c)(1),
(2) Date: Jun. 19, 2019

(87) PCT Pub. No.: WO2018/117338
PCT Pub. Date: Jun. 28, 2018

(65) Prior Publication Data
US 2019/0328250 A1 Oct. 31, 2019

(30) Foreign Application Priority Data
Dec. 19, 2016 (KR) .......................... 10-2016-0173985

(51) Int. Cl.
*A61N 1/05* (2006.01)
*A61B 5/24* (2021.01)
(Continued)

(52) U.S. Cl.
CPC .............. *A61N 1/0556* (2013.01); *A61B 5/24* (2021.01); *B41M 3/006* (2013.01);
(Continued)

(58) Field of Classification Search
CPC .............. A61B 5/24; A61B 2562/0215; A61B 2562/125; A61B 2562/164; A61N 1/0051;
(Continued)

(56) References Cited

U.S. PATENT DOCUMENTS 6,564,079 B1 * 5/2003 Cory ...................... A61B 5/282
600/397
8,845,950 B2 * 9/2014 Park ........................ H01M 4/96
264/29.7

(Continued)

FOREIGN PATENT DOCUMENTS

EP        2767632 A1 *  8/2014  .............. A61B 5/25
JP     2014-055119 A     3/2014
(Continued)

OTHER PUBLICATIONS

Huaiqiang Yu et al., "A Parylene Self-Locking Cuff Electrode for Peripheral Nerve Stimulation and Recording", Journal of Microelectromechanical Systems, Oct. 2014, pp. 1025-1035, vol. 23, No. 5.
(Continued)

*Primary Examiner* — Brian K Talbot
(74) *Attorney, Agent, or Firm* — NKL Law; Jae Youn Kim

(57) ABSTRACT

The present invention relates to a method of manufacturing a nerve electrode in which a conductive ink is inkjet printed on an electrospun polyimide fibrous sheet; and a nerve electrode manufactured by the manufacturing method.

7 Claims, 16 Drawing Sheets

(51) Int. Cl.
- B41M 3/00 (2006.01)
- B41M 5/00 (2006.01)
- D01D 5/00 (2006.01)
- D01F 6/74 (2006.01)

(52) U.S. Cl.
CPC ........ B41M 5/0023 (2013.01); B41M 5/0047 (2013.01); B41M 5/0064 (2013.01); D01D 5/0007 (2013.01); D01F 6/74 (2013.01); *A61B 2562/0215* (2017.08); *A61B 2562/125* (2013.01); *A61B 2562/164* (2013.01); *D10B 2509/00* (2013.01)

(58) Field of Classification Search
CPC .. B41M 3/006; B41M 5/0023; B41M 5/0047; B41M 5/0064; D01D 5/007; D01F 6/74; D04H 1/728; B05D 1/26; B05D 3/0254; B05D 5/12
USPC ........................................................ 600/377
See application file for complete search history.

(56) References Cited

U.S. PATENT DOCUMENTS

| | | | | |
|---|---|---|---|---|
| 9,061,137 | B2* | 6/2015 | Lee | A61N 1/0556 |
| 2002/0095080 | A1* | 7/2002 | Cory | A61B 5/282 |
| | | | | 600/393 |
| 2007/0239245 | A1* | 10/2007 | Borgaonkar | A61N 1/0565 |
| | | | | 607/121 |
| 2011/0139331 | A1* | 6/2011 | Arora | H01M 10/0585 |
| | | | | 264/109 |
| 2011/0307042 | A1* | 12/2011 | DeCarmine | A61N 1/0553 |
| | | | | 29/841 |
| 2012/0148896 | A1* | 6/2012 | Dennes | H01G 11/52 |
| | | | | 361/500 |
| 2013/0078527 | A1* | 3/2013 | Lee | D01D 5/0038 |
| | | | | 264/465 |
| 2014/0154594 | A1* | 6/2014 | Lee | H01M 8/102 |
| | | | | 429/408 |
| 2014/0167329 | A1* | 6/2014 | L'Abee | B29C 71/02 |
| | | | | 264/114 |
| 2015/0125665 | A1* | 5/2015 | Nakase | B32B 5/145 |
| | | | | 156/308.6 |
| 2015/0152232 | A1* | 6/2015 | Ju | C08J 5/18 |
| | | | | 524/442 |
| 2015/0183931 | A1* | 7/2015 | Fujii | C09D 179/08 |
| | | | | 528/353 |
| 2016/0164057 | A1* | 6/2016 | Arora | H01M 10/0525 |
| | | | | 429/163 |
| 2016/0175748 | A1* | 6/2016 | Park | B29C 48/142 |
| | | | | 427/458 |
| 2016/0198570 | A1* | 7/2016 | Yonezawa | B32B 15/20 |
| | | | | 428/209 |
| 2017/0182751 | A1* | 6/2017 | Du | B32B 27/12 |
| 2017/0326381 | A1* | 11/2017 | Kozai | A61N 1/0551 |

FOREIGN PATENT DOCUMENTS

| | | |
|---|---|---|
| JP | 5450885 B2 | 3/2014 |
| KR | 10-0925757 B1 | 11/2009 |
| KR | 20110129110 A * | 12/2011 |
| KR | 10-2014-0046709 A | 4/2014 |
| KR | 10-2015-0048935 A | 5/2015 |
| KR | 10-2015-0070468 A | 6/2015 |
| KR | 10-2016-0084428 A | 7/2016 |
| KR | 10-2016-0107527 A | 9/2016 |

OTHER PUBLICATIONS

Guo et al., "Stretchable Polymeric Multielectrode Array for Conformal Neural Interfacing", Communication, 2014, pp. 1427-1433, vol. 26.

McClain et al., "Highly-compliant, microcable meuroelectrodes fabricated from thin-film gold and PDMS", Biomed Microdevices, Jan. 15, 2011, pp. 361-373, vol. 13.

Machhi, "Finite Element Analysis of the Nerve Cuff to Determine Usability and Stress Analysis During Regular Use", Project, pp. 1-26.

Shih et al., "Yield strength of thin--film parylene-C", Microsystem Technologies, 2004, pp. 407-411.

Al-Halhouli et al., "Nanoindentation testing of SU-8 photoresist mechanical properties", Microelectronic Engineering, Oct. 4, 2007, pp. 942-944, vol. 85.

Rosset et al., "Flexible and stretchable electrodes for dielectric elastomer actuators", Materials Science Processing, 2012, pp. 281-307, vol. 110.

Gao et al., "Changes in nerve microcirculation following peripheral nerve compression", Neural Regeneration Research, Apr. 2013, pp. 1041-1047, vol. 8, Issue 11.

* cited by examiner

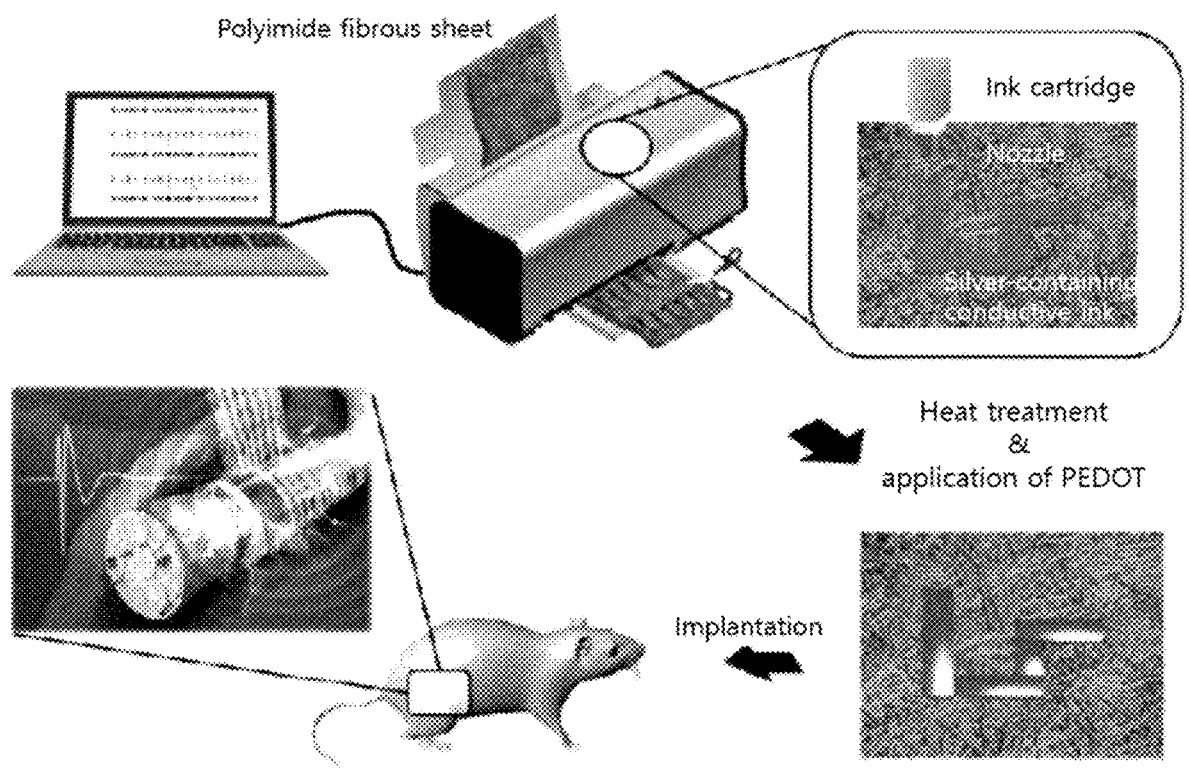
FIG. 2
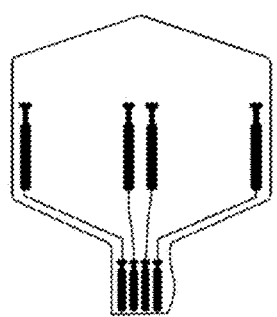 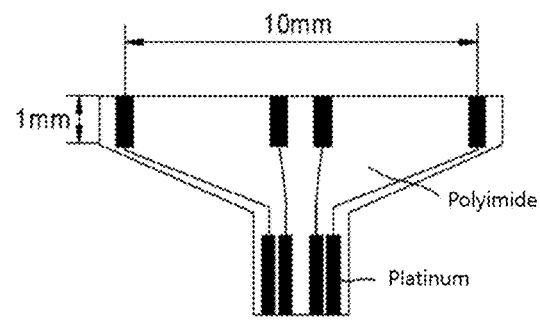
FIG. 3A  FIG. 3B

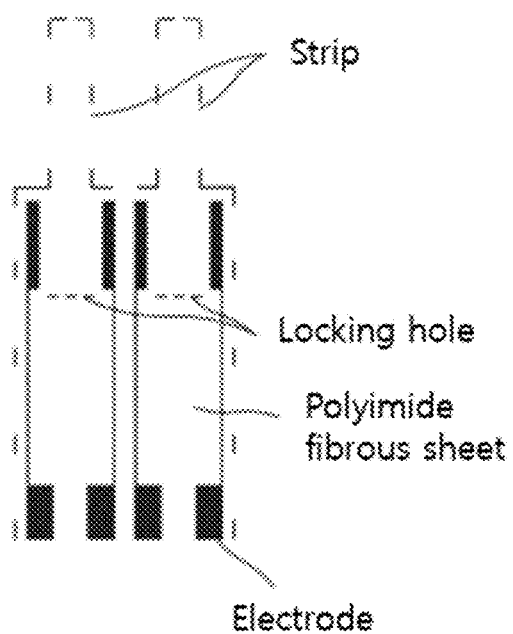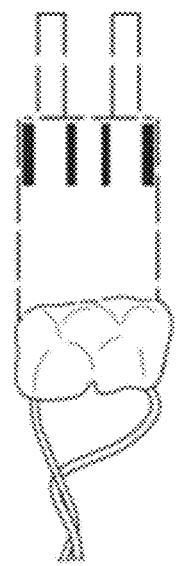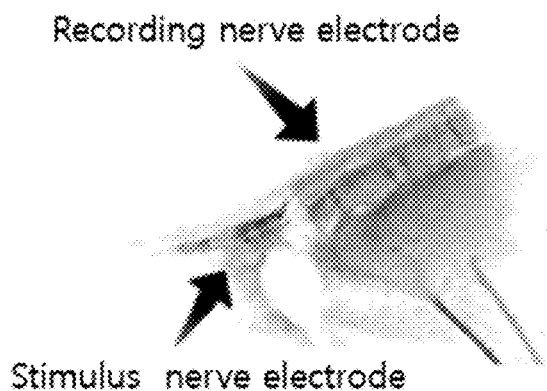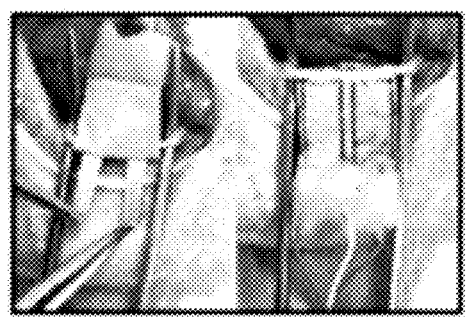
FIG. 4A  FIG. 4B
FIG. 4C  FIG. 4D

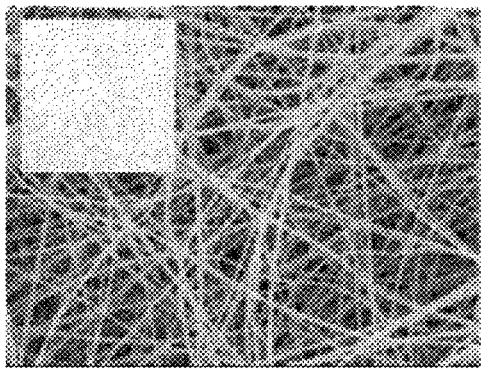 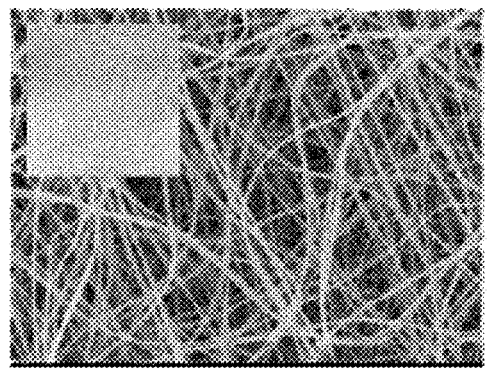
FIG. 5A  FIG. 5B
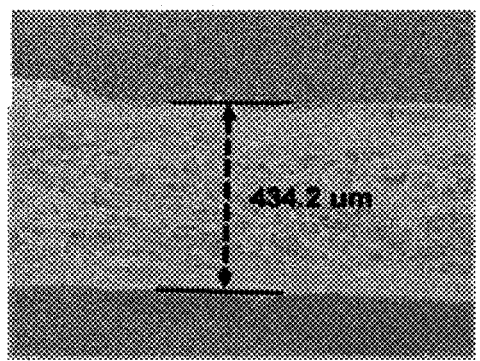 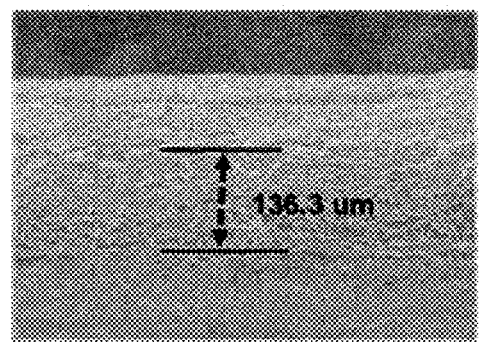
FIG. 6A  FIG. 6B

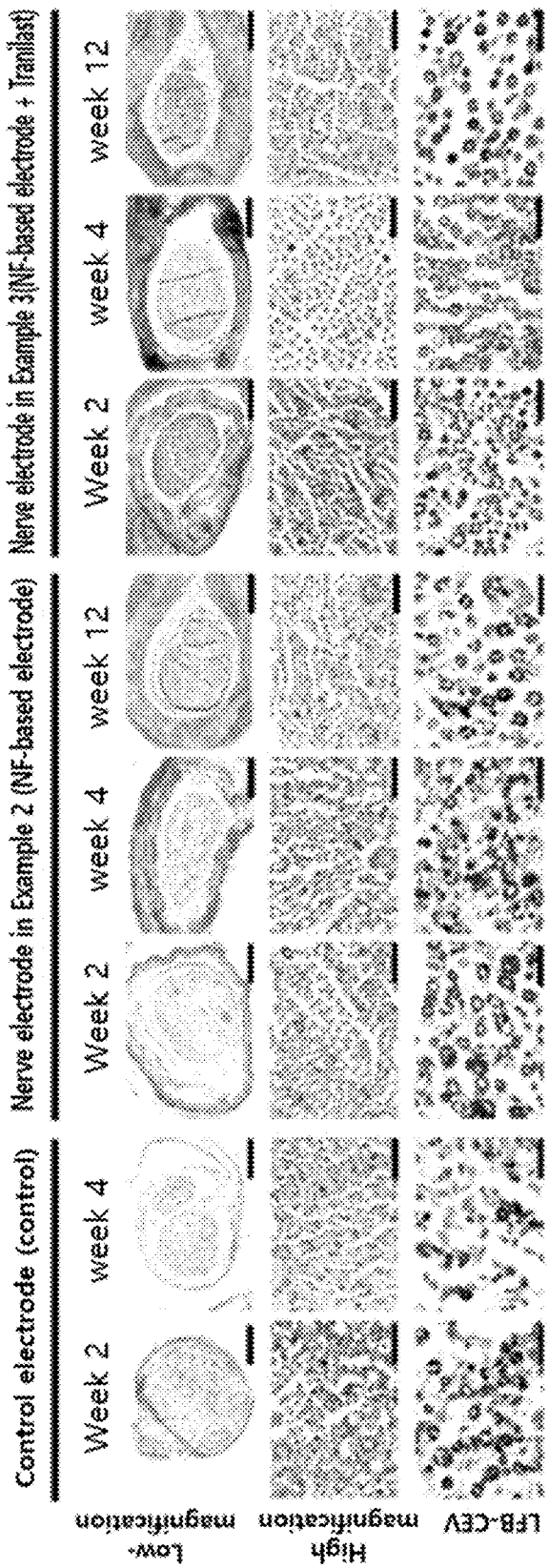
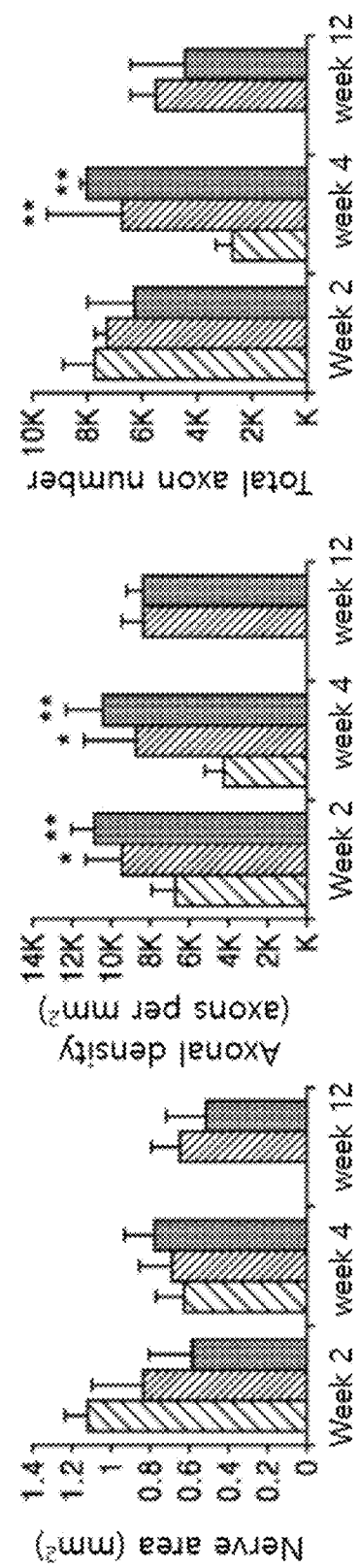
FIG. 20A
FIG. 20B

METHOD OF MANUFACTURING NERVE ELECTRODE

TECHNICAL FIELD

The present invention relates to a method of manufacturing a nerve electrode which has high permeability and flexibility and is excellent in biocompatibility, and a nerve electrode manufactured by the manufacturing method.

BACKGROUND ART

Many biomedical devices such as a cardiac pacemaker, a cochlear implant, and a prosthetic device require a small electrode that may react with nerve cells. Further, these electrodes have been used for treatment of patients with neurological diseases such as spinal cord injury, stroke, and degenerative disease by providing the recording of nerve signals and the activation of the nervous system.

Since nerve electrodes are implanted in the body, when nerve electrodes are implanted into nerve tissue, nerve electrodes need to cause less mechanical mismatching with the nerve tissue and need not cause a secondary disease by compressing nerve tissues, and require characteristics in which a phenomenon such as degeneration caused by nerve cell ischemia, Schwann cell necrosis, and nerve fiber deformation needs to be minimized. Nerve electrodes for satisfying these requirements are largely classified into two types, one is an invasive microneedle-type nerve electrode that penetrates the nerve bundle, and the other is a non-invasive cuff-type nerve electrode that surrounds the nerve trunk.

The invasive microneedle-type nerve electrode has an advantage in that the accessibility and selectivity for nerve cells to be measured are high and the nerve electrical signals can be recorded in a state where the stimulus intensity is reduced. However, these invasive nerve electrodes have a disadvantage in that nerve tissues may be damaged after implantation and wounds may be aggravated by the invasive nerve electrodes. Meanwhile, in the cuff-type nerve electrode, a flexible polymer substrate is used. Since cuff-type nerve electrodes are more bio-friendly than invasive microneedle-type nerve electrodes and easy to adhere close to various forms of nerves, tissue damage is relatively less and longer nerve information can be exchanged than invasive microneedle-type nerve electrodes, so that the cuff-type nerve electrodes have an advantage in that a successful interfacing with the peripheral nervous system can be achieved.

When the non-invasive cuff-type nerve electrode is placed on the nerve trunk and records nerve electrical signals by direct contact, nerve electrodes having a relatively inflexible structure cause biological problems such as inflammation, formation of fibrotic tissues, vascular constriction, and neurological atrophy. In order to alleviate these problems, a nerve electrode to which a more flexible substrate replacing an existing silicon substrate is applied was proposed, and Parylene C, polydimethylsiloxane (PDMS), and the like have been applied. As an example, when a self-locking cuff-type nerve electrode employing parylene as a substrate and consisting of a line and a locking loop is used, it has been reported that the nerve electrode is easily implanted into neurons and the shrinkage of the nerve trunk is not caused during an implantation period of 11 weeks or more. In addition, in order to obtain a more flexible cuff-type nerve electrode and minimize the difference in mechanical strength between physical contact regions, a nerve electrode employing polydimethylsilixane (PDMS) as a substrate has been reported.

However, when compared with actual nerve tissues, the above-described nerve electrode employing a polymer as a substrate is still not flexible, and the Young's modulus range of the nerve electrode is still high. Specifically, among the nerves of the human body, the Young's moduli of the brain, the spinal cord, and the peripheral nerve are 2.7 to 3.1 kPa, 3 to 6.3 kPa, and to 6.3 kPa, respectively. However, polymeric substrates such as silicon, polydimethylsiloxane (PDMS), Parylene C, and SU-8, which have been currently used as a substrate of a nerve electrode are not as flexible as actual nerve tissues because the Young's moduli of the polymeric substrates show a value ranging from 1.0 MPa to 8.45 GPa.

Furthermore, metallic elements including gold, stainless steel, platinum, titanium, and iridium contained in a polymeric substrate impart a stiffness effect during their deposition on the substrate and cause a problem in that the devices prevent the nerve electrode from completely conforming to the nerve trunk because the Young's moduli of the metallic devices range from 74 GPa to 530 GPa.

Therefore, the present inventors completed a nerve electrode which has high permeability and flexibility and is excellent in biocompatibility in order to ameliorate the problems as described above.

PRIOR ART DOCUMENTS

Non-Patent Documents

1. Yu, H., et al., J. Microelectromech. Syst. 23, 10251035 (2014).
2. Guo, L., Ma, M., et al., Adv. Mater. 26, 14271433 (2013).
3. McClain, M. A. et al., Biomed Microdevices 13, 361373 (2011).
4. Machhi, V. Finite Element Analysis of the Nerve Cuff to Determine Usability and Stress Analysis During Regular Use (2013).
5. Shih, C. Y. et al., Microsystem Technologies 10, 407411 (2004).
6. Al-Halhouli et al., Microelectronic Engineering 85, 942944 (2008).
7. Roseset, Applied Physics A 110, 281-307, 36 (2013).
8. Gao, Y., et al., Neural regeneration research 8, 1041 (2013).

DISCLOSURE

Technical Problem

An object of the present invention is to provide a method of manufacturing a nerve electrode which has high permeability and flexibility and is highly biocompatible, and thus can sense nerve signals stably for a long period of time.

Another object of the present invention is to provide a nerve electrode manufactured by the manufacturing method.

Technical Solution

In order to accomplish the above objects, the present invention provides a method of manufacturing a nerve electrode, the method including the steps of:

1) manufacturing a poly(amic acid) fibrous sheet by electrospinning poly(amic acid);

2) manufacturing a polyimide fibrous sheet by heat-treating the poly(amic acid) fibrous sheet;

3) thermally compressing the polyimide fibrous sheet;

4) inkjet printing a conductive ink on the polyimide fibrous sheet thermally compressed in Step 3); and 5) heat-treating the polyimide fibrous sheet on which the conductive ink is inkjet printed in Step 4).

The method of manufacturing a nerve electrode of the present invention is schematically illustrated in FIG. 1.

In the present invention, Step 1) is a step of manufacturing a fibrous sheet consisting of poly(amic acid) fibers by electrospinning poly(amic acid).

In the present invention, the poly(amic acid) may be commercially available or synthesized by a publicly known method. For example, the poly(amic acid) may be synthesized by reacting anhydride with a diamine.

The anhydride may be, for example, any one or more selected from the group consisting of pyromellitic dianhydride (PMDA), phthalic anhydride (PA), 3,3'4,4'biphenyl-tertracarboxylic dianhydride (BPDA), 4'-4-oxydiphthalic anhydride (ODPA), 3,3 '4,4'-benzophenonetetracarboxylic dianhydride (BTDA), trimellitic ethylene glycol (TMEG), 4,4'-(4'4-isopropylbiphenoxy)biphthalic anhydride (BPADA), perfluoroisopropylidene-containing acid dianhydride (6FDA) or trimellitic anhydride (TMA).

Further, the diamine may be, for example, any one or more selected from the group consisting of 4,4'-oxydianiline (4,4'-ODA), p-phenyl diamine (p-PDA), 2,2-bis(4-(4-aminophenoxy)-phenyl)propane (BAPP), p-methylenedianiline (p-MDA), propyltetramethyl disiloxane (GAPD), jeffamine (polyaromatic amine), 4,4'-diaminodiphenylsulfone (DDS), 2,2'-bis(trifluoromethyl)-4,4'-diaminobiphenyl (TFDB) or 3,5-diamino-1,2,4-triazole (Triazole).

In a preferred embodiment of the present invention, the poly(amic acid) may be synthesized by polycondensation of pyromellitic dianhydride (PMDA) and 4,4'-oxydianiline in N,N-dimethylacetamide.

In the present invention, the electrospinning may be performed by a well-known method in the art, and for example, may be performed by filling a supply device with a object to be spun, connecting an electrospinning nozzle to the supply device, and then using a high-voltage generation device between the nozzle and a current collector to form a high electric field. The magnitude of the electric field is related to the distance between the nozzle and the current collector, and the relationship between these two is used in combination to facilitate electrospinning. In this case, as an electrospinning device to be used, those typically used in the art may be used.

A nano-sized fiber structure may be synthesized by the electrospinning, and a fibrous sheet of the electrospun fibers as described above is highly biocompatible because the fibrous sheet is thinner, more porous, and more flexible than existing fibrous sheets.

In the present invention, it is preferred that a supply device is filled with the poly(amic acid) to be electrospun in the form of a solution, but the filling form is not limited thereto.

In the present invention, the electrospinning may be performed at a voltage of preferably 10 kV to 40 kV, and more preferably 12 kV to 24 kV. In the present invention, the voltage of the electrospinning and the distance between the nozzle and the current collector may be appropriately adjusted by those skilled in the art in order to form a preferred fibrous sheet.

In the present invention, the poly(amic acid) fiber synthesized by electrospinning may have a diameter of 500 to 1,500 nm, preferably 700 nm to 1,300 nm.

In a specific example of the present invention, a poly(amic acid) fibrous sheet was manufactured by putting a poly(amic acid) solution into a glass syringe and supplying a voltage of 18 kV to subject poly(amic acid) to electrospinning in a mandrel that is a current collector.

In the present invention, Step 2) is a step of manufacturing a polyimide fibrous sheet by applying heat to the fibrous sheet manufactured in Step 1) to imidize poly(amic acid).

The polyimide fibrous sheet has high thermal resistance, and thus is not deformed even though being heat-treated at high temperature.

In the present invention, a heat treatment temperature of the poly(amic acid) fibrous sheet may be 250° C. to 500° C., preferably 300° C. to 400° C., and the poly(amic acid) fibrous sheet may be heat-treated under dynamic or static temperature conditions.

In the present invention, a heat treatment time of the poly(amic acid) fibrous sheet may be 30 minutes to 6 hours, preferably 30 minutes to 3 hours.

In the present invention, a heat treatment of the poly(amic acid) fibrous sheet may be performed in a pressurized or non-pressurized state.

In the present invention, a heat treatment device of the poly(amic acid) fibrous sheet may be appropriately selected by those skilled in the art, and an oven or a furnace may be used in the heat treatment in a non-pressurized state, but the heat treatment device is not limited thereto.

The polyimide fibrous sheet manufactured in Step 2) of the present invention may have a thickness of 100 µm to 1,000 µm, preferably 200 µm to 600 µm, and more preferably 300 µm to 500 µm.

In a specific example of the present invention, a polyimide fibrous sheet was manufactured by heat-treating the poly(amic acid) fibrous sheet at 350° C. in an oven for 1 hour.

Step 3) of the present invention is a step of thermally compressing the polyimide fibrous sheet manufactured in Step 2) by applying heat and pressure to the fibrous sheet.

In the present invention, the step of thermally compressing the polyimide fibrous sheet may decrease the thickness of the polyimide fibrous sheet, decrease the roughness by enhancing surface flatness, and obtain a high printing quality when a conductive ink is inkjet printed.

In the present invention, the thermal compression may be performed at a temperature of 80° C. to 160° C., preferably 90° C. to 140° C. under a pressure of 500,000 N/m² to 1,000,000 N/m², preferably 600,000 N/m² to 900,000 N/m². The temperature and the pressure may be a dynamic or static condition.

In the present invention, the thermal compression may be performed for preferably 30 minutes to 6 hours, and more preferably 30 minutes to 3 hours.

In the present invention, a thermal compression device (Powerpress Heat Press, HP230B) may be appropriately selected by those skilled in the art, and for example, a flat-type press and a roll press may be used, but the thermal compression device is not limited thereto.

The polyimide fibrous sheet manufactured in Step 3) of the present invention may have a thickness of 50 µm to 300 µm, preferably 80 µm to 200 µm, and more preferably 100 µm to 160 µM.

In a preferred example of the present invention, the polyimide fibrous sheet manufactured in Step 2 while being pressurized for 30 minutes by using a heat press apparatus at 120° C. under a pressure of 600,000 N/m² was thermally compressed.

In specific experimental examples of the present invention, as a result of measuring the thickness and porosity of the polyimide fibrous sheet manufactured in Step 2), the polyimide fibers had a diameter of 628 nm to 1,156 nm and a porosity of 81.2 vol %. Further, in a specific experimental example of the present invention, as a result of measuring the thickness and porosity of the polyimide thermally compressed in Step 3), the thermally compressed polyimide fibrous sheet had a thickness of 125.5 μm to 147.1 μm and a porosity of 74.0 vol %.

Accordingly, it can be seen that the thickness of the polyimide fibrous sheet is decreased to ⅓ of the original thickness and the porosity thereof is reduced by only 7.2% by the thermal compression, and as a result, high porosity is maintained even after the thermal compression.

Step 4) of the present invention is a step of inkjet printing a conductive ink on the polyimide fibrous sheet.

In the present invention, the inkjet printing refers to the application of a predetermined pattern onto a substrate by spraying ink on the substrate. When the inkjet printing is used, an electrode may be formed on a substrate by simple equipment and a simple process.

The inkjet printing may be piezo-type, thermal jet-type, or bubble jet-type inkjet printing, but is not limited, and may be preferably piezo-type inkjet printing.

In the present invention, the inkjet printing may be performed repeatedly once to ten times, preferably twice to six times. The sheet resistance of the nerve electrode may be decreased by the repetition of the inkjet printing.

In a specific experimental example of the present invention, as a result of measuring the sheet resistance value according to the number of the conductive ink inkjet printings, it was confirmed that the sheet resistance when the inkjet printing was performed once was 3.6 ohm/sq, and the sheet resistance when the inkjet printing was performed repeatedly up to 6 times was decreased to 0.31 ohm/sq.

In the present invention, those skilled in the art may appropriately select a commercially available apparatus as an apparatus which performs the inkjet printing.

In the present invention, the conductive ink refers to an ink containing a conductive substance. The conductive substance may be preferably a metal nanoparticle, but is not limited thereto. The metal nanoparticle may be, for example, a silver nanoparticle, a gold nanoparticle, a copper nanoparticle, an aluminum nanoparticle, a platinum nanoparticle, a titanium nanoparticle, an iridium nanoparticle, or an indium nanoparticle, but is not limited thereto, and may be preferably a silver nanoparticle.

In the present invention, those skilled in the art may appropriately select a pattern on which a conductive ink is inkjet printed, and may input the pattern using a commercially available program.

In a specific example of the present invention, an ink containing silver nanoparticles was inkjet printed in the form and size of a pattern input through an AutoCAD program on a polyimide fibrous sheet.

In a specific experimental example of the present invention, as a result of confirming mechanical characteristics of the polyimide fibrous sheet on which the conductive ink containing silver nanoparticles was inkjet printed, it was confirmed that mechanical characteristics such as tensile stress and tensile modulus did not deteriorate due to the deposition of silver nanoparticles.

Step 5) of the present invention is a step of fusing the conductive ink which has been inkjet printed with the polyimide fibrous sheet by heat-treating the conductive ink.

Particles of the conductive ink are melted by the heat treatment, and the molten conductive ink may be fused with the fiber structure to more efficiently form an electrically connected structure in the polyimide fibrous sheet.

In the present invention, a heat treatment temperature of the polyimide fibrous sheet on which the conductive ink is inkjet printed may be 100° C. to 300° C., preferably 140° C. to 220° C., and the polyimide fibrous sheet may be heat-treated under dynamic or static temperature conditions.

In the present invention, a heat treatment time of the polyimide fibrous sheet on which the conductive ink is inkjet printed may be 30 minutes to 6 hours, more preferably 30 minutes to 3 hours.

In the present invention, a heat treatment of the polyimide fibrous sheet on which the conductive ink is inkjet printed may be performed in a pressurized or non-pressurized state.

In the present invention, a heat treatment device of the polyimide fibrous sheet on which the conductive ink is inkjet printed may be appropriately selected by those skilled in the art, and for example, the heat treatment may be performed in an oven.

In a specific example of the present invention, the polyimide fibrous sheet on which the conductive ink was inkjet printed was heat-treated at 180° C. in an air atmosphere for 1 hour.

Furthermore, in a preferred embodiment of the present invention, the manufacturing method of the present invention may further include 6) a step of applying poly(3,4-ethylene dioxythiophene)/poly(styrenesulfonate) (PEDOT/PSS) on the inkjet printed conductive ink by an electrochemical polymerization method.

The manufacturing method of the present invention may form a thin film having a uniform distribution and a uniform filling density by the application of the PEDOT/PSS, so that an active area of the surface of the nerve electrode is increased. Accordingly, an improved electrical connection between nerve signals and the nerve electrode may be secured.

In a specific experimental example of the present invention, it was confirmed that poly(3,4-ethylene dioxythiophene)/poly(styrenesulfonate) (PEDOT/PSS) was applied onto the inkjet printed conductive ink by electrochemical polymerization, and as a result, an effect of increasing the active surface area of the nerve electrode was obtained.

In a specific experimental example of the present invention, it was confirmed that a conductive polymer poly(3,4-ethylene dioxythiophene)/poly(styrenesulfonate) (PEDOT/PSS) was applied onto the inkjet printed conductive ink by electrochemical polymerization, and as a result, the electrical connectivity between nerve signals and the nerve electrode was improved.

In a preferred embodiment of the present invention, the manufacturing method of the present invention may further a step of containing an anti-fibrotic drug by bringing the nerve electrode manufactured by the manufacturing method including Steps 1) to 5) or the nerve electrode manufactured by the manufacturing method including Steps 1) to 6) into contact with a solution in which the anti-fibrotic drug is dissolved.

In the present invention, the bringing of the nerve electrode into contact with the solution includes completely immersing the nerve electrode in the solution, immersing only one surface of the nerve electrode in the solution, and applying the solution on one surface or both surfaces of the nerve electrode, and may include all other methods in which the solution may be brought into contact with the nerve electrode.

In the present invention, the anti-fibrotic drug may be an anti-fibrotic drug known to those skilled in the art, and may be preferably one or more anti-fibrotic drugs selected from the group consisting of tranilast, mitomycin, pirfenidone, ibuprofen, aztreonam, tobramycin, and ciprofloxacin, and more preferably tranilast.

In a specific experimental example of the present invention, it could be confirmed that the nerve electrode in which tranilast was contained exhibited less expression of fibrotic tissues in a site where the nerve electrode was implanted, had less axonal degeneration, and maintained a better axonal structure than a nerve electrode in which tranilast was not contained.

Further, in a specific experimental example of the present invention, as a result of measuring the signal to noise ratio of the nerve electrode in which tranilast was contained and the nerve electrode in which tranilast was not contained, it could be seen that there was no big difference in signal to noise ratio in both the nerve electrodes.

Accordingly, it can be seen that the nerve electrode in which the anti-fibrotic drug is contained, which is manufactured by the manufacturing method of the present invention, is excellent in biocompatibility.

The present invention provides a nerve electrode manufactured by the method of manufacturing a nerve electrode.

The nerve electrode is the same as those described previously.

The nerve electrode of the present invention is thin and flexible, has good elasticity, and is highly biocompatible due to the excellent porosity and permeability. Further, the mechanical strength such as tensile stress and tensile modulus is also excellent.

The nerve electrode of the present invention specifically refers to a cuff-type electrode. The polyimide fibers included in the nerve electrode of the present invention may have a diameter of 600 nm to 1,200 nm, preferably 700 nm to 1,300 nm.

The polyimide fibrous sheet included in the nerve electrode of the present invention may have a porosity of 60 vol % to 90 vol %, preferably 65 to 85 vol %.

In a preferred embodiment of the present invention, the nerve electrode may include an anti-fibrotic drug.

In the present invention, the anti-fibrotic drug may be an anti-fibrotic drug known to those skilled in the art, and may be preferably one or more anti-fibrotic drugs selected from the group consisting of tranilast, mitomycin, pirfenidone, ibuprofen, aztreonam, tobramycin, and ciprofloxacin, and more preferably tranilast.

The anti-fibrotic drug included in the nerve electrode of the present invention may be present in an amount of 0.1 wt % to 20 wt %, preferably 0.1 wt % to 1 wt % based on a total weight of the nerve electrode.

The nerve electrode of the present invention may be for sensing nerve signals, and the sensing of nerve signals may be sensing of nerve signals of a nervous system selected from the group consisting of an electrocardiograph, electroencephalograph, electromyograph, electroretinograph, and transcutaneous nerve graph, but is not limited thereto.

In the present invention, the sensing of nerve signals refers to confirmation of whether nerve signals occur, and includes recording characteristics including the magnitude, duration time, and the like of nerve signals occurred.

Advantageous Effects

The manufacturing method of the present invention can manufacture a nerve electrode which is thin, excellent in porosity and permeability, flexible and elastic, and also excellent in mechanical strength such as tensile stress and tensile modulus. In addition, the manufacturing method of the present invention can manufacture a nerve electrode which has a low impedance and also a very low signal to noise ratio, and may sense nerve signals stably for a long period of time. Furthermore, the nerve electrode by the manufacturing method of the present invention has remarkably decreased inflammation response, cellular infiltration, axonal atrophy, fibrosis of nerve cells, and the like as compared to existing nerve electrodes.

DESCRIPTION OF DRAWINGS

FIG. 2 is a conceptual view of a process for the method of manufacturing a nerve electrode of the present invention.

FIGS. 3A and 3B illustrate a nerve electrode employing a polyimide film manufactured in the Comparative Example of the present invention as a substrate.

FIGS. 4A, 4B, 4C and 4D illustrate the design and application of the nerve electrode manufactured by the manufacturing method of the present invention, where FIG. 4A is a structural view of the design, FIG. 4B is a photograph of the nerve electrode actually commercialized according to the structural view of FIG. 4A, FIG. 4C is a photograph illustrating the application of the nerve electrode of FIG. 4B to an actual nerve tissue, and FIG. 4D is a photograph illustrating the application of the nerve electrode of FIG. 4B to nerve tissues of a mouse.

FIGS. 5A and 5B are images of a fibrous sheet manufactured in an Example of the present invention captured by scanning electron microscopy, where FIG. 5A is a poly (amic acid) fibrous sheet, and FIG. 5B is a polyimide fibrous sheet.

FIGS. 6A and 6B are the measurements of the thicknesses of the polyimide fibrous sheets manufactured in the Examples of the present invention, where FIG. 6A illustrates the fibrous sheet of Example 1-2, and FIG. 6B illustrates the fibrous sheet of Example 1-3.

FIG. 9A is a polyimide fibrous sheet manufactured in Example 1-4 of the present invention, FIG. 9B is a nerve electrode manufactured in Example 1-5 of the present invention, FIG. 9C is an enlarged image of FIG. 9B, and FIG. 9D is an image of the nerve electrode in Example 2.

manufactured in Example 1-2 of the present invention and the polyimide film (PI film) manufactured in the Comparative Example of the present invention.

Figure 12:
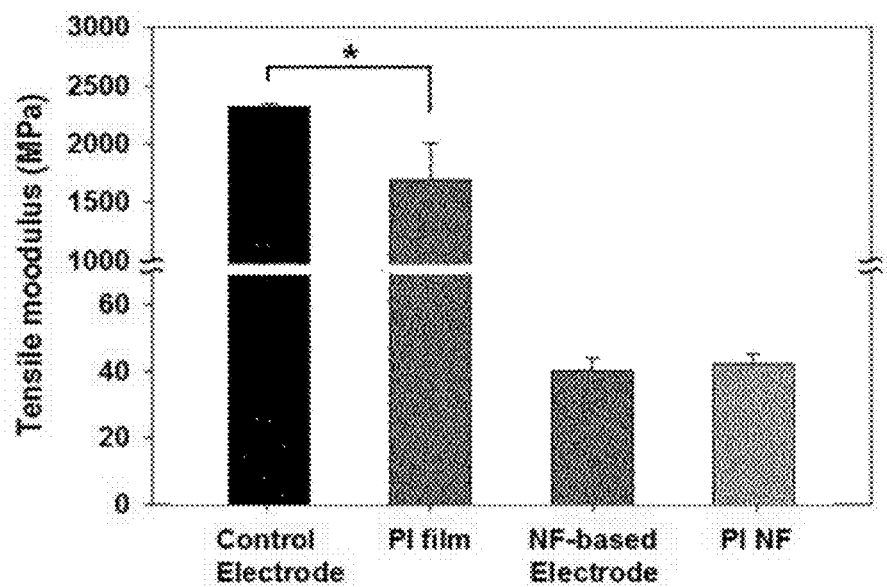

FIG. 12 is a graph illustrating the tensile moduli of the polyimide fibrous sheet (PI NF) manufactured in Example 1-2 of the present invention, the nerve electrode (NF-based electrode) manufactured in Example 1-5 of the present invention, the polyimide film (PI film) manufactured in the Comparative Example, and a control electrode in which a platinum electrode is deposited onto the polyimide film manufactured in the Comparative Example of the present invention.

Figure 13:
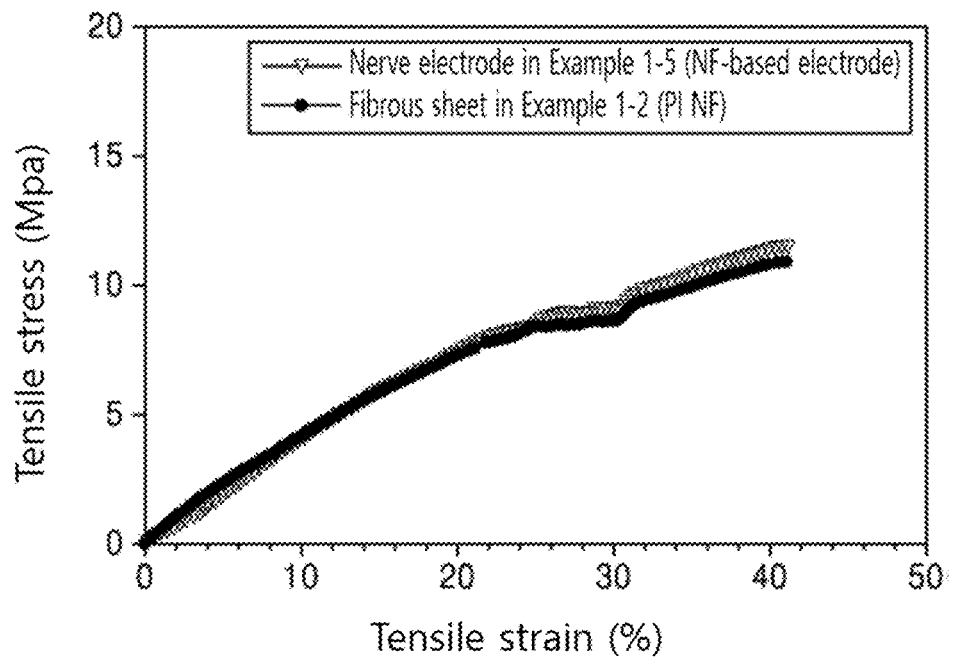

FIG. 13 is a graph illustrating the tensile stresses of the polyimide fibrous sheet (PI NF) manufactured in Example 1-2 of the present invention and the nerve electrode (NF-based electrode) manufactured in Example 1-5 of the present invention.

Figure 14:
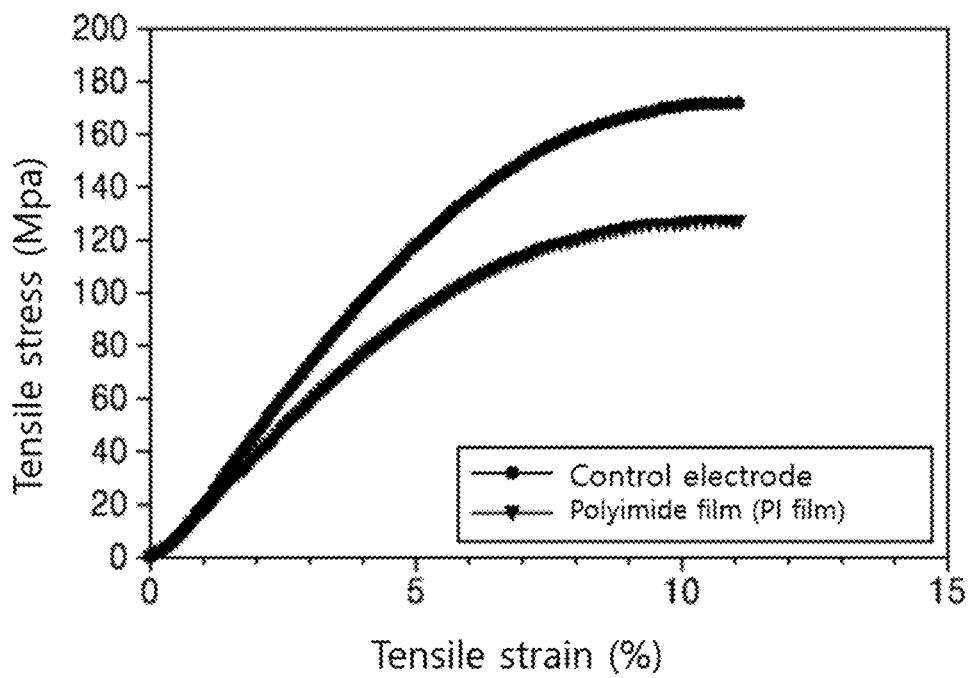

FIG. 14 is a graph illustrating the tensile stresses of the polyimide film (PI film) manufactured in the Comparative Example and the control electrode in which a platinum electrode is deposited onto the polyimide film manufactured in the Comparative Example.

Figure 15:
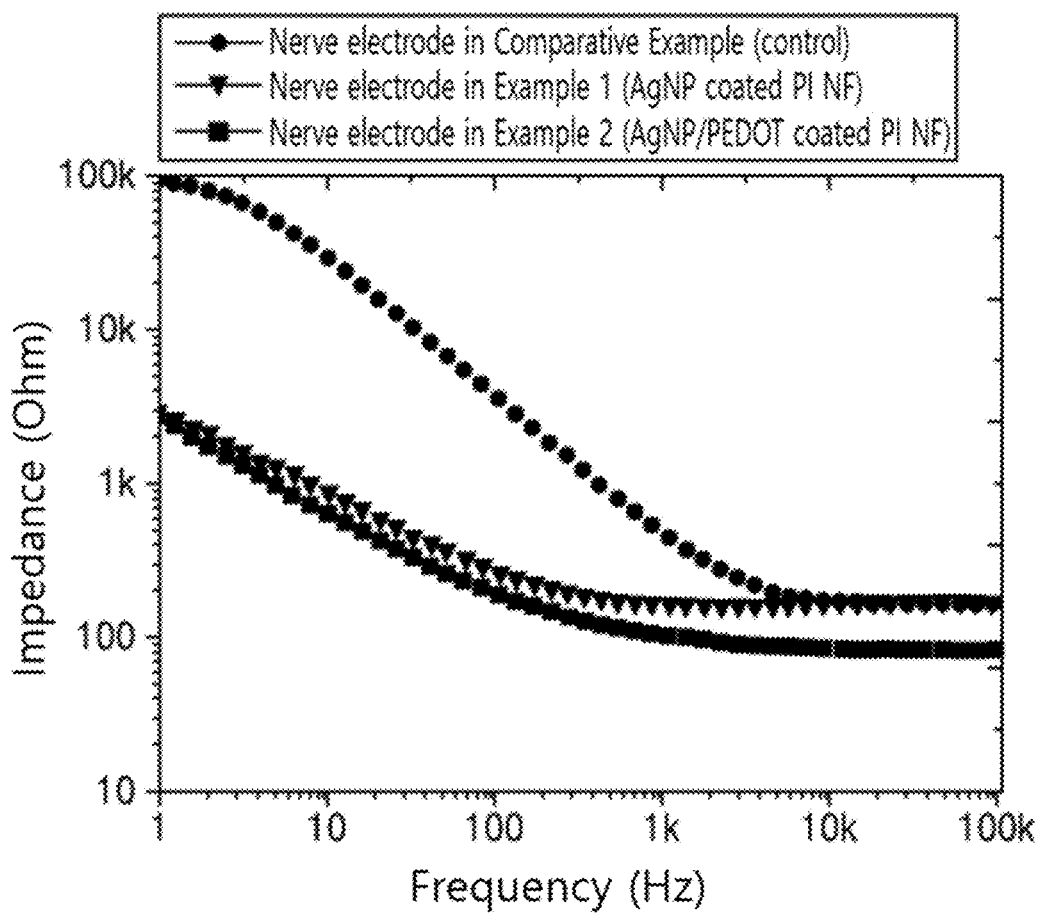

FIG. 15 is a graph illustrating the electrochemical impedances of the nerve electrode (AgNP coated PI NF) manufactured in Example 1 of the present invention, the nerve electrode (AgNP/PEDOT coated PI NF) manufactured in Example 2 of the present invention, and the nerve electrode (control) manufactured in Comparative Example 1 of the present invention.

Figure 16:
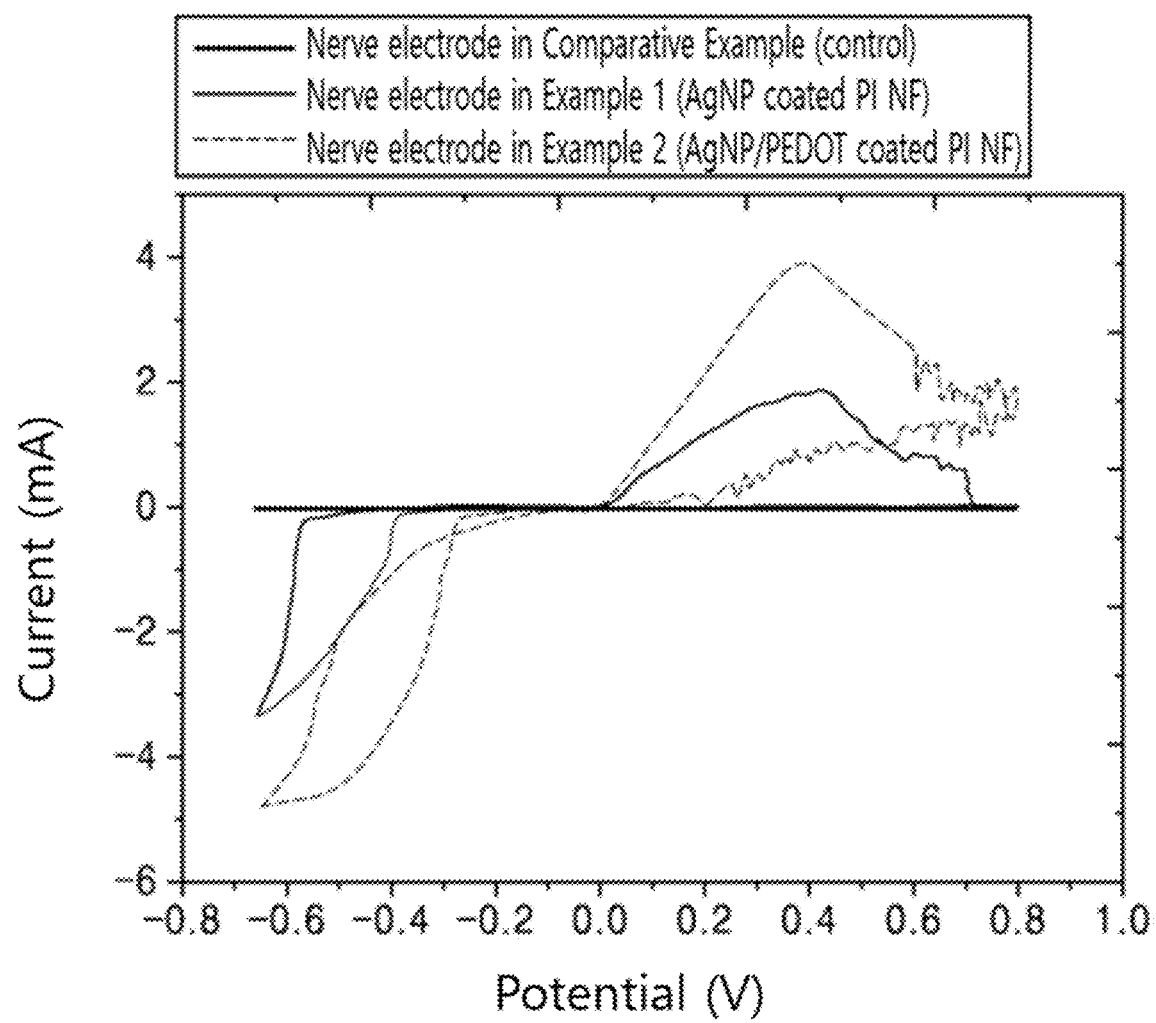

FIG. 16 is a graph illustrating a cyclic voltage-current curve (cyclic voltammetry) of the nerve electrode (AgNP coated PI NF) manufactured in Example 1 of the present invention, the nerve electrode (AgNP/PEDOT coated PI NF) manufactured in Example 2 of the present invention, and the nerve electrode (control) manufactured in the Comparative Example of the present invention.

Figure 17A:
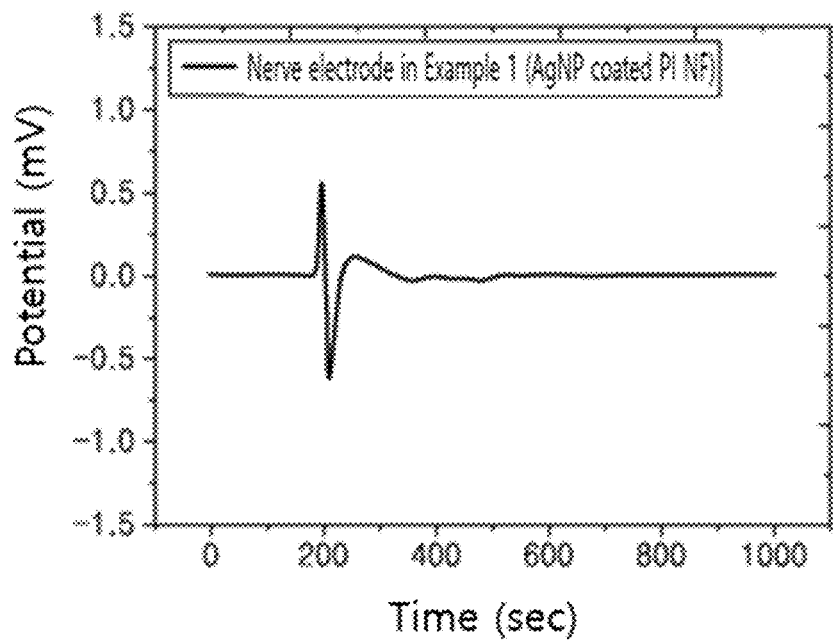
Figure 17B:
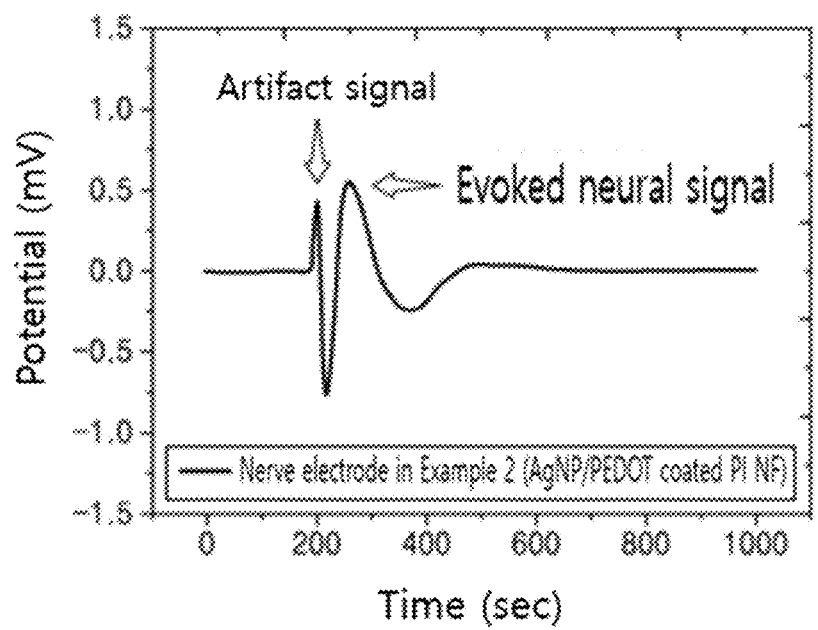

FIG. 17A and 17B are graphs illustrating signal recordings when the nerve electrodes manufactured in the Examples of the present invention are applied to mouse sciatic nerves, where FIG. 17A illustrates signals of the nerve electrode manufactured in Example 1, and FIG. 17B illustrates signals of the nerve electrode manufactured in Example 2.

Figure 18:
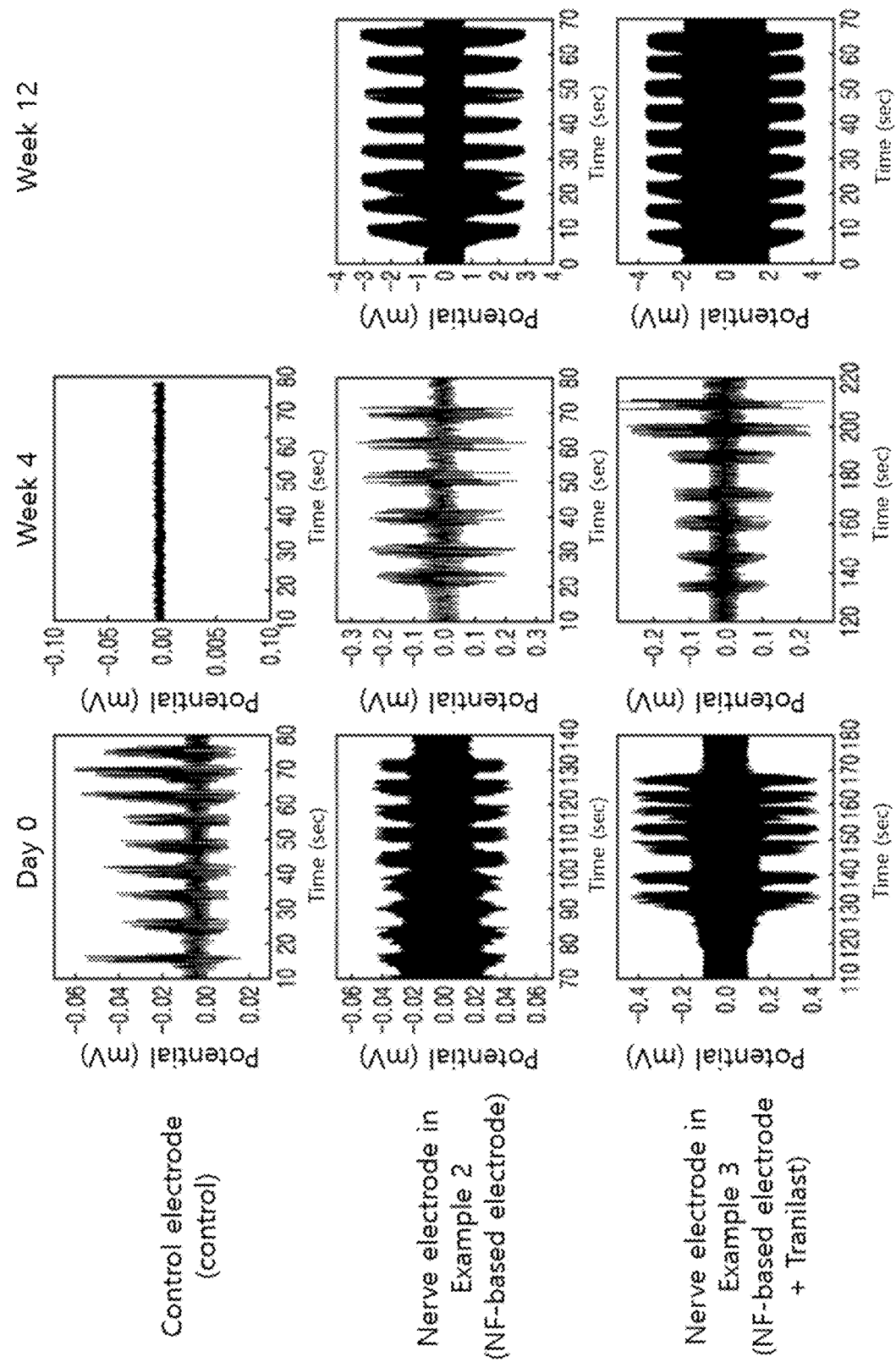

FIG. 18 is a graph illustrating recordings of signals of electroneurograms (ENGs) of the nerve electrode (NF-based electrode) manufactured in Example 2 of the present invention, the nerve electrode (NF-based electrode+Tranilast) manufactured in Example 3 of the present invention, and the nerve electrode (control) manufactured in the Comparative Example of the present invention.

Figure 19:
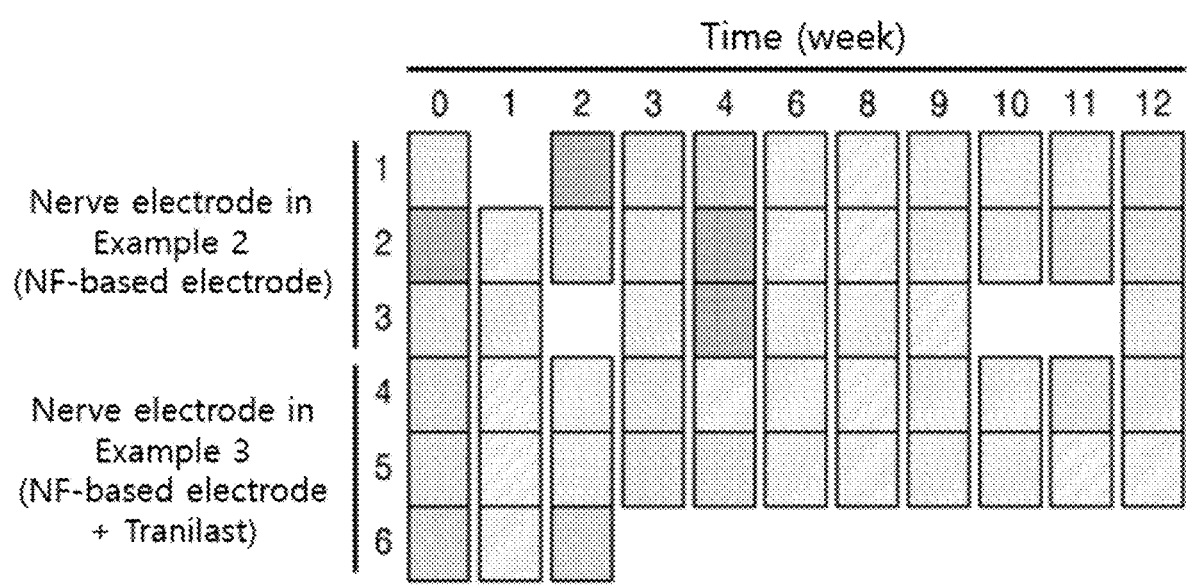

FIG. 19 illustrates the signal to noise ratio (SNRs) measured in rats into which the nerve electrode (NF-based electrode) manufactured in Example 2 of the present invention and the nerve electrode (NF-based electrode+Tranilast) manufactured in Example 3 of the present invention are implanted, as a heapmap.

FIG. 20A is an observation of tissues when the nerve electrode (NF-based electrode) manufactured in Example 2 of the present invention, the nerve electrode (NF-based electrode+Tranilast) manufactured in Example 3 of the present invention, and the nerve electrode (control) manufactured in the Comparative Example of the present invention are implanted into the sciatic nerves of rats, and FIG. 20B is a set of graphs illustrating the nerve area, axonal density, and total axonal number thereof.

MODES OF THE INVENTION

Hereinafter, preferred examples and experimental examples for helping the understanding of the present invention will be suggested. However, they are provided only to more easily understand the present invention, and the scope of the present invention is not limited by the following contents.

Figure 1:
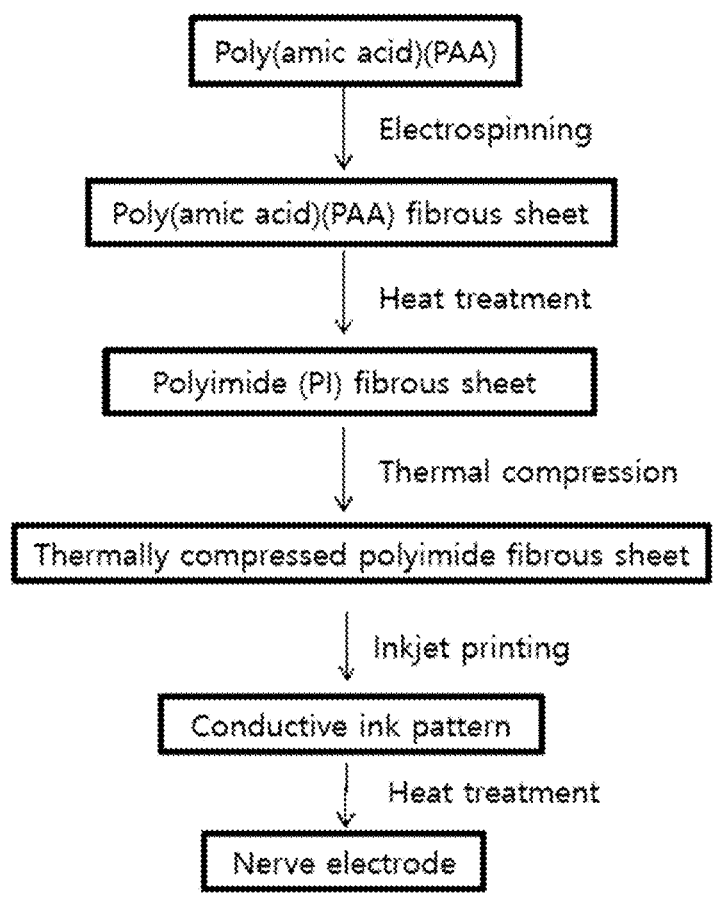
FIG. 1 is a process flowchart according to a method of manufacturing a nerve electrode of the present invention.

<Example 1> Manufacture of Nerve Electrode Employing Polyimide Fibrous Sheet as Substrate According to the manufacturing process disclosed in FIG. 1, a nerve electrode employing a polyimide fibrous sheet as a substrate was manufactured. FIG. 2 illustrates a conceptual view of the method of manufacturing a nerve electrode according to the present invention.

1-1. Manufacture of Poly(Amic Acid) Fibrous Sheet

After 33.4688 g of N,N-dimethylacetamide and 4.0048 g of 4,4'-oxydianiline were completely dissolved using an overhead stirrer (PL-SS20D), poly(amic acid)(PAA) was synthesized by slowly adding 4.3624 g of pyromellitic dianhydride (PMDA) thereto and stirring the resulting mixture under a low temperature condition (ice bath, 4° C.) overnight for polycondensation.

Thereafter, a poly(amic acid) solution was put into a 10-ml glass syringe equipped with an 18-gauge needle (Kovax-needle, Korea), and electrospun on the surface of a rotating mandrel displaying a voltage of 18 kV at a flow rate of 1.0 ml/h using a syringe pump (KD-200, KD Scientific, USA). The distance between the nozzle and the mandrel was kept at 15 cm, and a high-voltage DC power supply (Nano Nc, Korea) was used as an apparatus. Poly(amic acid) electrospun in a fiber state was stacked on the mandrel, thereby manufacturing a poly(amic acid) fibrous sheet.

1-2. Manufacture of Polyimide Fibrous Sheet

Poly(amic acid) was imidized by heat-treating the poly (amic acid) fibrous sheet manufactured in Example 1-1 at 350° C. in an air atmosphere in an oven (Electric furnace, CRF M13.P) for 1 hour. As a result, a polyimide fibrous sheet was formed.

1-3. Thermal Compression of Polyimide Fibrous Sheet

After the polyimide fibrous sheet manufactured in Example 1-2 was naturally cooled, the polyimide fibrous sheet was thermally compressed under a pressure of 600,000 N/m$^2$ at 120° C. by a thermal press apparatus (Powerpress Heat Press, HP230B).

1-4. Inkjet Printing of Conductive Ink

A conductive ink containing silver nanoparticles was inkjet printed by employing the polyimide fibrous sheet manufactured in Example 1-3 as a substrate.

The conductive ink was allowed to be automatically supplied to an inkjet printer (EPSON C88+) through an ink cartridge (JS-B25P, NovaCentrix Co.). In order to form an inkjet printed conductive ink, the conductive ink was inkjet printed according to a pattern set by the AutoCAD program. The polyimide fibrous sheet was supplied through a paper feed rack of the inkjet printer.

After a conductive ink containing silver nanoparticles was inkjet printed once on the polyimide fiber, the conductive ink was inkjet printed repeatedly up to six times on the same position.

1-5. Manufacture of Nerve Electrode Employing Polyimide Fiber as Substrate

The polyimide fibrous sheet inkjet printed in Example 1-4 was heat-treated at 180° C. in an air atmosphere in an oven (Electric furnace, CRF M13.P) for 1 hour.

<Example 2> Manufacture of Nerve Electrode Further Including PEDOT/PSS Layer

A conductive polymer poly(3,4-ethylene dioxythiophene)/poly(styrenesulfonate) (PEDOT/PSS) was applied onto the nerve electrode manufactured in Example 1 by an electrochemical polymerization method.

Specifically, a PEDOT/PSS solution was prepared by adding 0.01 M 3,4-ethylene dioxythiophene (EDOT)(Sigma Aldrich, Saint Louis, Mo., USA) and 0.1 M poly(sodium 4-styrenesulfonate) (PSS)(Sigma Aldrich, Saint Louis, Mo., USA) to 100 ml of triple-distilled water. An electrochemical polymerization was performed in the galvanostatic mode using Autolab PGSTAT 302N (EcoChemie, Utrecht, Netherlands), and a general tri-electrode configuration was used. A working electrode was connected to a line electrode position of a functional nerve cuff electrode through an external connection terminal. An Ag/AgCl electrode was used as a reference electrode, and a platinum line was used as a counter electrode. A current density of $8\mu\mu A/mm^2$ was applied to each line electrode for 300 seconds.

As a result, poly(3,4-ethylene dioxythiophene)/poly(styrenesulfonate) (PEDOT/PSS) was applied onto silver nanoparticles of the nerve electrode manufactured in Example 1.

<Example 3> Manufacture of Nerve Electrode Containing Anti-Fibrotic Drug

Tranilast (2 mg) was dissolved in ethanol (1 mL). 200 μL of this solution was applied onto the nerve electrode manufactured in Example 2, and dried under an air condition. As a result, 150 to 300 μm of tranilast was contained in the nerve electrode.

<Comparative Example> Manufacture of Nerve Electrode Employing Polyimide Film as Substrate A polyimide solution (PI, VTEC PI-1338) was spin-coated on a silicon wafer having a thickness of 20 μm. Thereafter, a polyimide film was manufactured by curing the silicon wafer coated with polyimide at 90° C. for 10 minutes, at 110° C. for 10 minutes, and 220° C. for 60 minutes in a convection oven (JEIO Tech Co., Ltd., Daejeon, Korea).

Thereafter, a negative photoresist (DNR-L300-30, Dongjin, Seoul, Korea) and a Ti/Pt (50/300 nm) layer were patterned by a lift-off process.

A second polyimide layer was spin-coated on silicon wafer having a thickness of 5 μm for insulation treatment, and cured in acetone. An electrode portion was exposed by coating the second polyimide layer with a positive photoresist (AZ 9260, AZ Electronic Materials, New Jersey, USA), a micro-well was made, and then holes were produced using a reactive ion etching (Plasma-Therm, St. Petersburg, Fla., USA) method, thereby completing a nerve electrode employing a polyimide film as a substrate. The nerve electrode is illustrated in FIG. 3.

The electrode employing a polyimide film as a substrate may be cut by a laser cutter (M-2000, Exitech, Oxford, UK) and used.

<Reference Example> Design and Application of Nerve Electrode for being Applied to Nerve Fibers The nerve electrodes manufactured in Examples 1 to 3 were designed as illustrated in FIG. 4A.

Specifically, a locking hole was made and a strip for adjusting the length was formed on a polyimide fibrous sheet. Moreover, an electric wire cable was connected to an end opposite to the strip using a conductive epoxy bond, and the surface thereof was closed with bone cement. The appearance of the manufactured cuff-type nerve electrode is the same as that illustrated in FIG. 4B.

As illustrated in FIG. 4C and FIG. 4D, the nerve electrode may be used to stimulate or sense nerve signals by surrounding nerve tissues and putting the strip into the locking hole to fix the nerve electrode.

<Experimental Example 1> Structural Analysis of Poly(Amic Acid) Fibrous Sheet and Polyimide Fibrous Sheet 1-1. Morphological Analysis of Poly(Amic Acid) Fibrous Sheet and Polyimide Fibrous Sheet The morphologies of the poly(amic acid) fibrous sheet manufactured in Example 1-1 and the thermally compressed polyimide fibrous sheet manufactured in Example 1-3 were observed by scanning electron microscopy (hereinafter, referred to as SEM) (Hitachi S-4700). All samples were sputtered by a platinum sputtering device for 10 minutes and prepared.

As a result, the poly(amic acid) fibers had a diameter of 1,023±272 nm, and the polyimide fibers had a diameter of 892±264 nm. Further, the morphologies of the surfaces of the poly(amic acid) fibrous sheet and the polyimide fibrous sheet observed by the SEM are the same as that illustrated in FIG. 5A and FIG. 5B, respectively.

In addition, as illustrated in FIG. 6, the fibrous sheet in Example 1-2 had a thickness of 434.2±18.6 μm, and the fibrous sheet in Example 1-3 had a thickness of 136.3±10.8 μm.

1-2. Chemical Structural Analysis of Poly(Amic Acid) Fibrous Sheet and Polyimide Fibrous Sheet The chemical structures of the poly(amic acid) fibrous sheet manufactured in Example 1-1 and the polyimide fibrous sheet manufactured in Example 1-2 were confirmed by attenuated total reflectance Fourier-transform infrared Spectroscopy (Perkin-Elmer, Spectrum™ ONE System).

Figure 7:
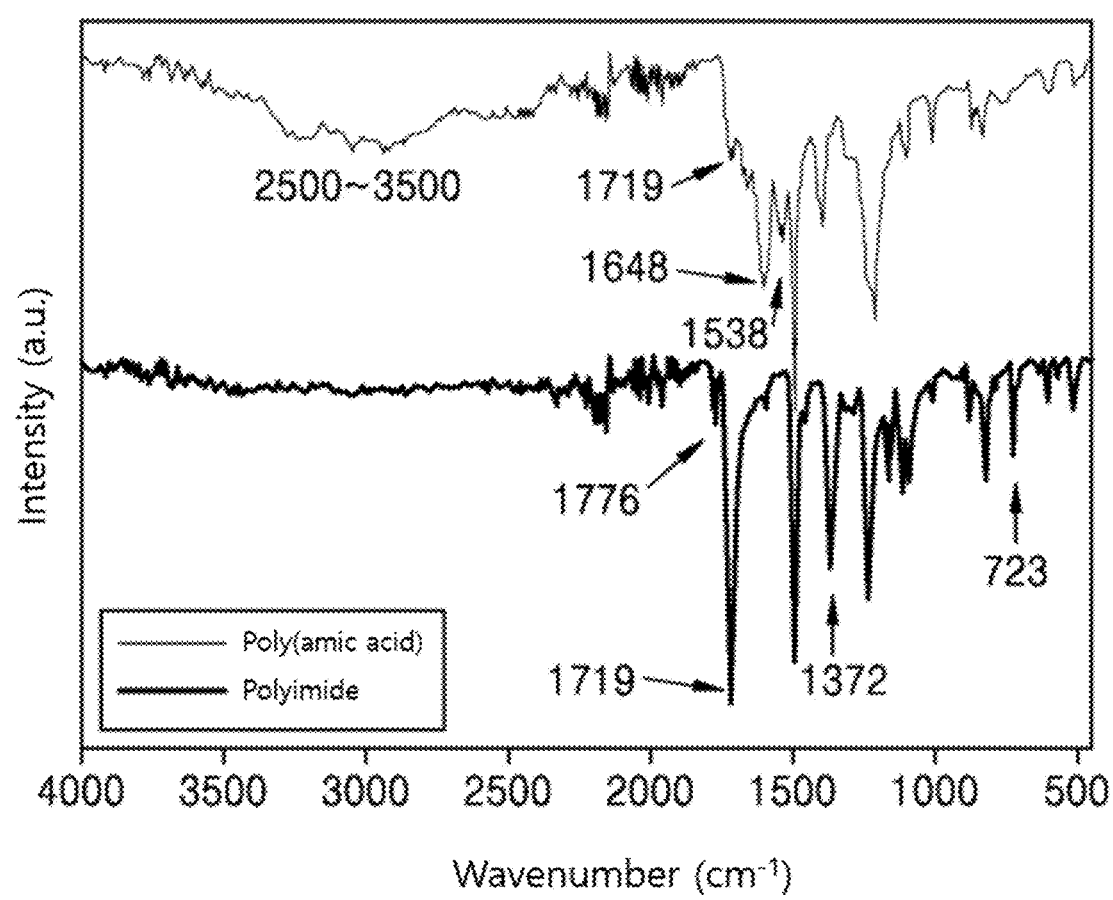
FIG. 7 is a graph illustrating Fourier-transform infrared spectroscopy (FT-IR) results of the poly(amic acid) fibrous sheet manufactured in Example 1-1 of the present invention and the polyimide fibrous sheet manufactured in Example 1-2 of the present invention.

As a result, as illustrated in FIG. 7, the poly(amic acid) fibrous sheet showed a peak corresponding to amine and carboxylic acid functional groups at 3430 $cm^{-1}$, a peak corresponding to an amide I functional group at 1648 $cm^{-1}$, and a peak corresponding to an amide II functional group at 1538 $cm^{-1}$. However, these peaks disappeared in the spectrum of the polyimide fibrous sheet, and new peaks such as 1776 $cm^{-1}$ (C=O symmetric stretching), 1371 $cm^{-1}$ (C—N stretching), and 723 $cm^{-1}$ (C=O bending) appeared.

Accordingly, it can be confirmed that the poly(amic acid) fibrous sheet used in the present invention is imidized.

<Experimental Example 2> Measurement of Sheet Resistance of Inkjet Printed Pattern While the ink containing silver nanoparticles was inkjet printed repeatedly up to six times on the polyimide fibrous sheet manufactured in Example 1-3, the sheet resistance value according to the repetition number was each measured by an SRM 4-point probe sheet resistance meter (SRM-232-2000).

Figure 8:
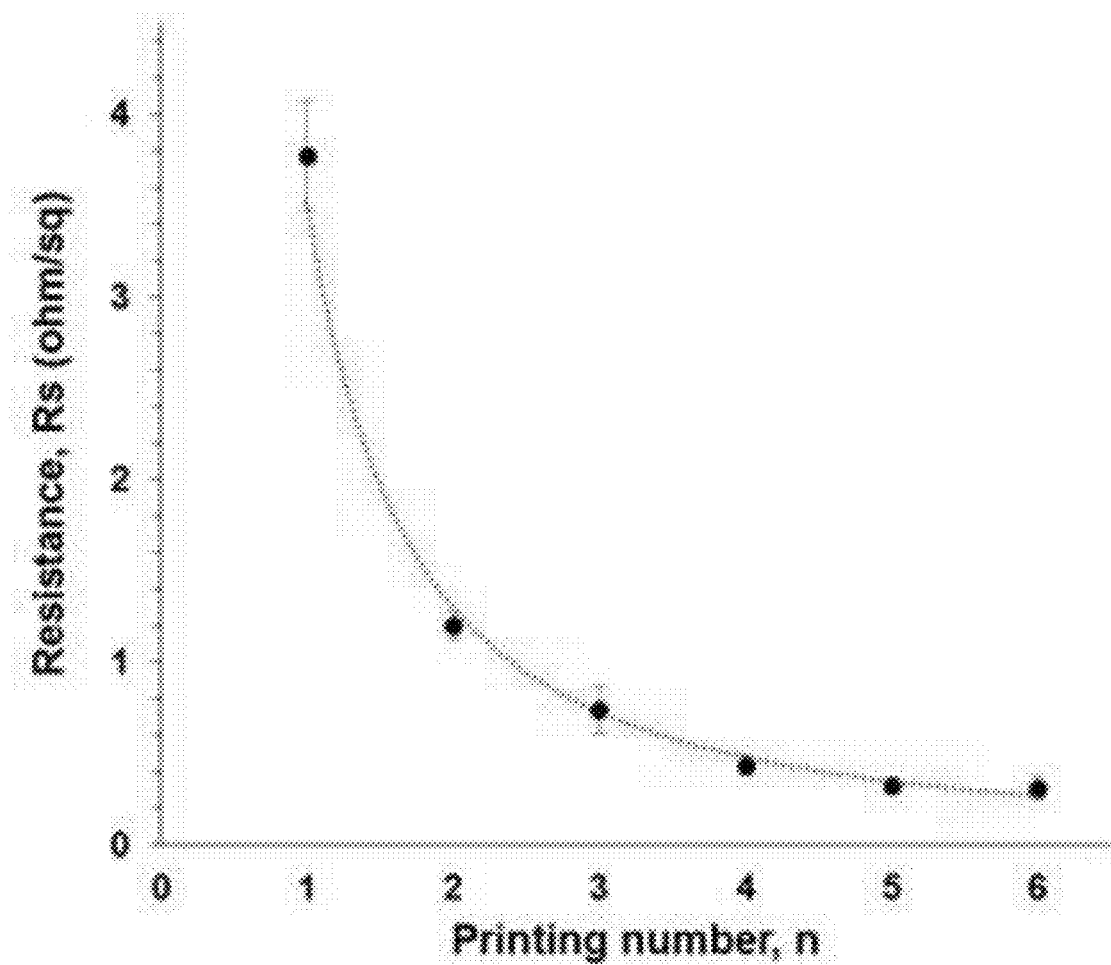
FIG. 8 is a graph illustrating the relationship between the inkjet printing number of the conductive ink containing silver nanoparticles and the sheet resistance in Example 1-4 of the present invention.

As a result, as illustrated in FIG. 8, it could be confirmed that the sheet resistance was decreased from 3.6 ohm/sq to 0.31 ohm/sq according to the inkjet printing number, and it could be confirmed that the sheet resistance was rapidly decreased even when the inkjet printing was performed only twice.

Accordingly, it can be seen that the resistance by the ink including metal nanoparticles may be significantly decreased by the repetition of the inkjet printing.

<Experimental Example 3> Structural Analysis of Nerve Electrode of Present Invention The morphologies of the inkjet printed polyimide fibrous sheet manufactured in Example 1-4 of the present invention, the nerve electrode manufactured in Example 1-5, and the nerve electrode in Example 2 were observed by SEM (Hitachi S-4700), and the results thereof are illustrated in FIG. 9.

Figures 9A, 9B, 9C, 9D:
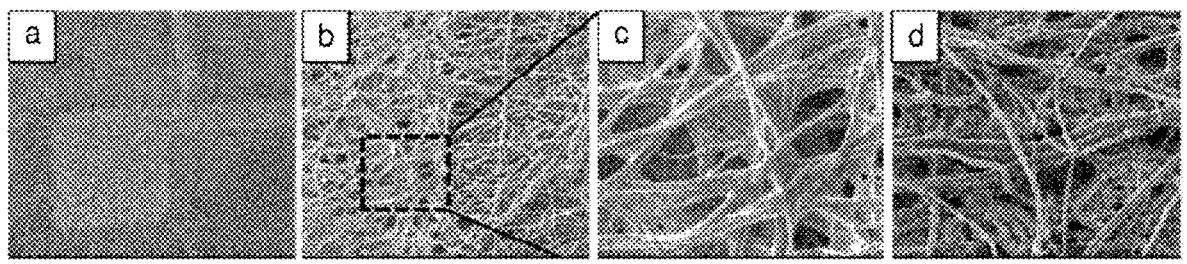
FIGS. 9A, 9B, 9C and 9D are images of the fibrous sheet or nerve electrodes manufactured in the Examples of the present invention observed by scanning electron microscopy, where

FIG. 9A is an image of the inkjet printed polyimide fibrous sheet manufactured in Example 1-4 of the present invention, FIG. 9B is an image of the nerve electrode manufactured in Example 1-5, and FIG. 9C is an enlarged image of FIG. 9B. When FIGS. 9A to 9C are compared with one another, it can be confirmed that as a result of the heat treatment of the fibrous sheet in Example 1-4, silver nanoparticles are fused with the sheet.

Furthermore, FIG. 9D is an image of the nerve electrode in Example 2, and it can be confirmed that the PEDOT/PSS is uniformly deposited onto the polyimide fibrous sheet.

<Experimental Example 4> Measurement of Porosity of Nerve Electrode of Present Invention The porosities of the polyimide fibrous sheet of the present invention and the polyimide film manufactured in the Comparative Example were measured by a porosity analyzer (AutoPorelV 9500, Micrometrics Co.).

The porosity was measured by immersing the sample in mercury and applying various levels of pressures thereto.

Figure 10A:
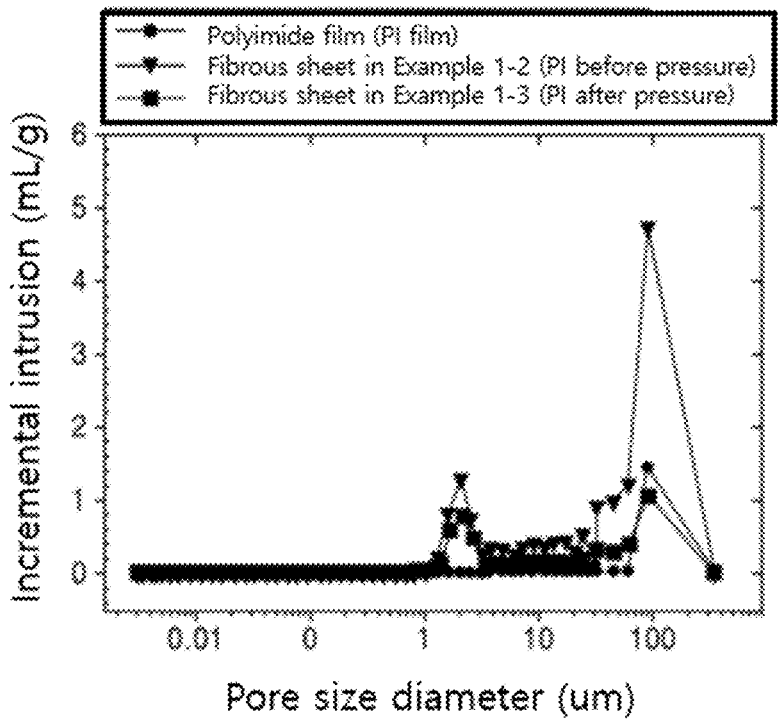
FIG. 10 is a set of graphs illustrating the porosities of the polyimide fibrous sheet (PI before pressure) manufactured in Example 1-2 of the present invention, the polyimide fibrous sheet (PI after pressure) manufactured in Example 1-3 of the present invention, and the polyimide film (PI film) manufactured in the Comparative Example of the present invention.
Figure 10B:
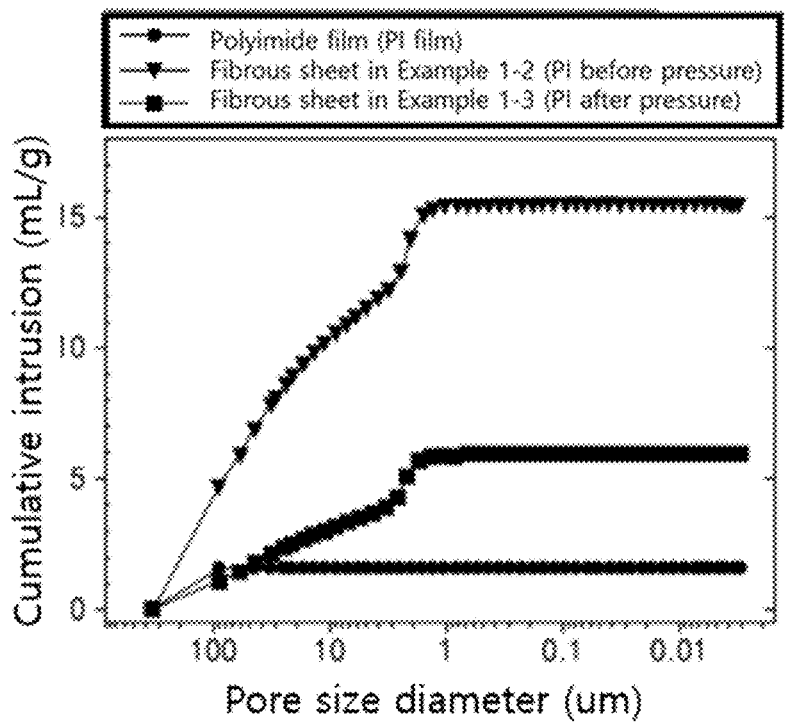

The results thereof are illustrated in FIGS. 10A and 10B. The porosity of the polyimide fibrous sheet manufactured in Example 1-2 was 81.2%, and the porosity of the polyimide fibrous sheet to which pressure was applied in Example 1-3 was 74.0%. That is, it can be confirmed that when the polyimide fibrous sheet manufactured in Example 1-2 is heat-treated, the porosity is decreased by 7.2%, but high porosity is still maintained. Further, it can be confirmed that high porosity is still maintained compared to that of the polyimide film manufactured in the Comparative Example.

Accordingly, it can be seen that the nerve electrode of the present invention is excellent in porosity and permeability, and thus is highly biocompatible.

<Example 5> Evaluation of Mechanical Strength of Nerve Electrode of Present Invention The mechanical strengths of the polyimide fibrous sheet prior to thermal compression (PI NF) manufactured in Example 1-2 of the present invention, the thermally compressed nerve electrode after inkjet printing (NF-based electrode) manufactured in Example 1-5, the polyimide film (PI film) manufactured in the Comparative Example, and a control electrode in which a platinum electrode is deposited onto the polyimide film manufactured in the Comparative Example were measured using a tensile test apparatus (Schimadzu, EZ-SX).

The ultimate tensile stress, elongation at break, stress at elongation, and tensile modulus measured are the same as those shown in the following Table 1.

TABLE 1

| | Ultimate tensile stress (MPa) | Elongation at break (%) | Stress at 5% elongation (MPa) | Tensile modulus (MPa) |
|---|---|---|---|---|
| Control Electrode | 173.4 ± 5.3 | 11.8 ± 0.8 | 117.9 ± 1.1 | 2357.9 ± 22.1 |
| Polyimide film (PI film) | 128.3 ± 11.5 | 12.1 ± 3.5 | 86.1 ± 16.3 | 1723.1 ± 325.3 |
| Nerve electrode (NF-based Electrode) in Example 1-5 | 10.8 ± 1.1 | 42.1 ± 2.5 | 2.1 ± 0.3 | 43.1 ± 3.2 |
| Fibrous sheet (PI NF) in Example 1-2 | 10.5 ± 0.9 | 40.3 ± 0.8 | 2.0 ± 0.2 | 41.0 ± 4.1 |

Figure 11:
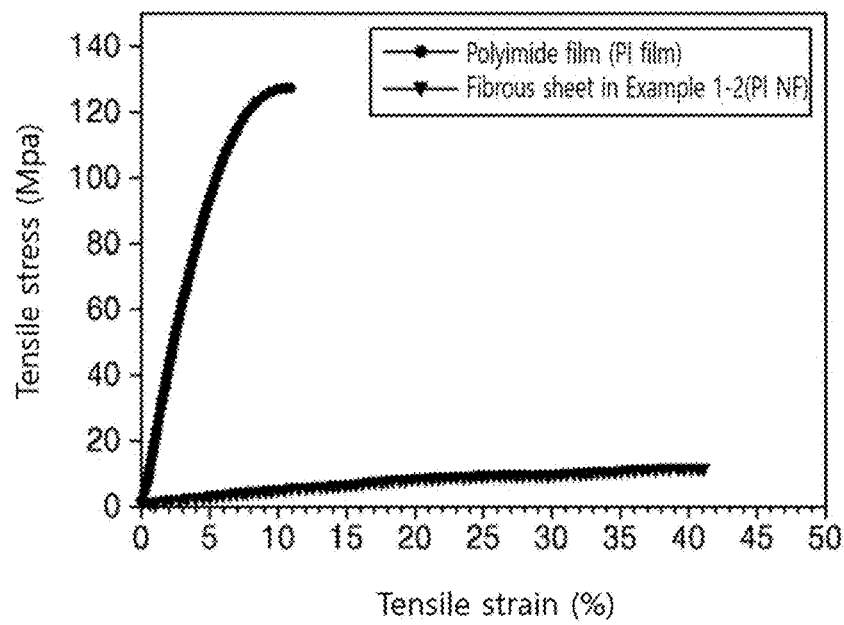
FIG. 11 is a graph illustrating the results of measuring the tensile stresses of the polyimide fibrous sheet (PI NF)

As illustrated in Table 1 and FIGS. 11 and 12, it can be seen that the polyimide film in the Comparative Example has an elongation of 12.1±3.5% and a tensile modulus of 1723.1±325.3 MPa, and thus has a very high stiffness, whereas the polyimide fibrous sheet in Example 1-2 of the present invention has an elongation of 40.3±0.8% and a tensile modulus of 41.0±4.1 MPa, and thus is much more flexible and elastic than the polyimide film in the Comparative Example.

In addition, as illustrated in Table 1 and FIG. 13, it was confirmed that even in the case of the nerve electrode in Example 1-5 in which the ink containing silver nanoparticles is inkjet printed on the polyimide fibrous sheet in Example 1-3 of the present invention, excellent mechanical characteristics are maintained. However, as illustrated in FIG. 14, in the case of the control electrode, mechanical characteristics such as ultimate tensile stress and tensile modulus were deteriorated more by the deposition of a tough metal than the polyimide film.

Accordingly, it can be seen that the while the nerve electrode of the present invention is flexible and elastic as it is, mechanical characteristics are not deteriorated even by the deposition of a conductive substance such as silver nanoparticles.

<Example 6> Evaluation of Electrochemical Characteristics of Nerve Electrode of Present Invention A cyclic voltage-current curve (cyclic voltammetry) for calculating the electrochemical impedance and charge delivery capacity (CDC) of the nerve electrode in Example 1 and the nerve electrode in Example 2 was measured, and the nerve electrode in the Comparative Example was used as the control electrode.

6-1. Measurement of Electrochemical Impedance

An electrochemical experiment of the nerve electrode was performed using an Autolab device (PGSTAT 302N, NOVA Software, Ecohemie, Netherlands), and 0.1 M physiological saline (pH 7.0) was used as an electrolyte of an electrochemical measurement system at room temperature. A commercially available tri-electrode system was installed for the measurement of impedance. The tri-electrode system in the present invention employed the nerve electrode in Example 1, the nerve electrode in Example 2, or the control electrode as a working electrode, a platinum wire as a counter electrode, and finally, an Ag/AgCl electrode as a reference electrode. As the platinum wire used as the counter electrode, a platinum wire manufactured with a purity of 99.95% and a size of 0.5 mm in diameter and 30 mm in length was used.

The frequency amplitude of the alternating current (AC) sine curve for the measurement of impedance may be established at 5 mV to 10 mV generally used in an electrochemical experiment, and in the present experiment, the impedance was measured at an alternating current magnitude of 10 mV in a frequency region of 1 to $10^5$ Hz.

As a result, as illustrated in FIG. 15, the nerve electrode in Example 1 exhibited an impedance value of 169Ω at 1 kHz, the nerve electrode in Example 2 exhibited an impedance value of 103Ω at 1 kHz, and the nerve electrode in the Comparative Example as the control electrode exhibited an impedance value of 516Ω at 1 kHz.

That is, it can be seen that the nerve electrode of the present invention has a much lower impedance value than the nerve electrode in the Comparative Example. Furthermore, it can be seen that when the PEDOT/PSS is deposited onto the nerve electrode, the widening of the surface active area of the nerve electrode increases the charge delivery capacity (CDC).

6-2. Measurement of Charge Delivery Capacity (CDC)

The result of measuring the cyclic voltage-current curve (cyclic voltammetry) after twenty repeated measurements was obtained as data in order to confirm that the double layer capacitance of the nerve electrode established as a working electrode was stabilized.

The measurement was performed between potential values established between the working electrode and the reference electrode at a potential scan rate of 100 mV/s, and in this case, the cyclic voltage-current curve (cyclic voltammetry) was measured by establishing the potential range at 0.65 V to 0.8 V so as not to include a potential value where water splitting in physiological saline used as an electrolyte occurs. The cyclic voltage-current curve is the same as that illustrated in FIG. 16.

The charge delivery capacity (CDC) was calculated using the following equation.

$$CDC = \frac{1}{vA} \int_{Ec}^{Ea} |i| dE (C/cm^2)$$

v: Potential scan rate (V/s),
A: Geometric surface area ($cm^2$) of the electrode,
Ea: Anodic potential limit
Ec: Cathodic potential limit
I: Measured current
E: Electrode potential (V vs Ag/AgCl)

As a result of calculating the charge delivery capacity from the cyclic voltage-current curve illustrated in FIG. 16, the calculated charge delivery capacity (CDC) measurement value possessed by the nerve electrode employing the fibrous sheet in Example 1 as the substrate was 116.08 $mC/cm^2$, the measurement value of the fibrous sheet in Example 2 was 183.37 $mC/cm^2$, and the measurement value of the commercially available cuff-type nerve electrode as the control electrode was 0.32 $mC/cm^2$, exhibiting the lowest value.

From the results described above, it can be seen that the nerve electrode of the present invention has better electrochemical characteristics than the commercially available cuff-type nerve electrode, and when the PEDOT/PSS is applied to the nerve electrode, a much better electrochemical interface can be formed.

<Experimental Example 7> Confirmation of Effect of Sensing Nerve Signals of Nerve Electrode of Present Invention 7-1. Ex-Vivo Experiment The nerve electrode in Example 1 of the present invention and the nerve electrode in Example 2 of the present invention were made into a design for the Reference Example, and used in an experiment.

10-week old male SD rats used in the present invention were raised in accordance with the regulations of the Institutional Animal Care and Use Committee (IACUC) of Konkuk University (KU16049), and disposed according to the purpose of the present invention. For the exact ex-vivo experiment, animals were sacrificed using carbon dioxide, and the sciatic nerves were collected. The incised sciatic nerves were immediately immersed in a Kreb's solution.

As illustrated in FIG. 4C, the nerve electrode in Example 1 or the nerve electrode in Example 2 was implanted as a recording nerve electrode that senses nerve signals. The recording nerve electrode records a nerve response to electrical signals applied from a stimulus nerve electrode. The stimulus nerve electrode and the record nerve electrode were implanted so as to surround nerves spaced apart from each other at an interval of 5 mm, and a ground electrode was connected so as to be immersed in the Kreb's solution.

Further, as illustrated in FIG. 4C, a stimulus cuff-type nerve electrode was implanted, and as the stimulus cuff-type nerve electrode, an electrode in which the width of the stimulus nerve electrode was reduced to ½ (5 mm) was used.

The stimulus nerve electrode was connected to a pulse stimulator (IsolatedPulse Stimulator, Model 2100, A-M Systems, Sequim, Wa, USA), and the recording nerve electrode was connected to a differential amplifier (Differential AC Amplifier, Model 1700, A-M system, Sequim, WA, USA). The amplified nerve signals of the sciatic nerves were collected using a data collection device (NI USB-6356, National Instruments, Seoul, Korea). In addition, the collected signals were monitored in a computer through LabVIEW software. With respect to the electrical stimulus, a pulse peak potential and a pulse duration were established at a magnitude of 300 μA and 100 μs, respectively.

As a result of measuring an evoked nerve compound action potential, that is, an evoked neural signal, induced by the application of biphasic pulse current, signals as illustrated in FIGS. 17A and 17B were recorded. FIG. 17A corresponds to a case where the nerve electrode in Example 1 is implanted as a recording nerve electrode, and FIG. 17B corresponds to a case where the nerve electrode in Example 2 is implanted as a recording nerve electrode.

The nerve electrode in Example 1 of the present invention exhibited a potential value of 0.151 mV as illustrated in FIG. 17A, and the nerve electrode in Example 2 of the present invention exhibited a potential value of 0.768 mV as illustrated in FIG. 17B.

Accordingly, it can be seen that the nerve electrode of the present invention may be usefully used for sensing nerve signals, and it can be seen that when the conductive polymer PEDOT/PSS is applied, the action potential value is significantly increased, and as a result, nerve signals may be more effectively sensed.

7-2. In-Vivo Experiment

The sensing of nerve signals was confirmed by implanting the nerve electrode in Example 2 of the present invention, the nerve electrode in Example 3, and the nerve electrode in the Comparative Example into Sprague Dawley (SD) rats, and as illustrated in FIG. 4A, the nerve electrode designed in the Reference Example was used. All the nerve electrodes were sterilized under a UV-sterilizer in a clean bench and exposed to a UV-C sterilization lamp (UV output: 19.8 W, Sankyo Denki, Japan) for 2 hours.

In order to perform an in-vivo experiment, anesthesia was induced by xylazine hydrochloric acid (HCl), and surgery was performed while the anesthesia state was maintained using 1.5 to 2% isoflurane with 100% 02.

The left sciatic nerves were exposed by incising the outer surface of the hind leg parallel to the femur, and the nerve electrode in Example 2 of the present invention, the nerve electrode in Example 3 of the present invention, and the nerve electrode in the Comparative Example of the present invention designed as in the Reference Example were implanted on the surface of the sciatic nerve of the SD rat as illustrated in FIG. 4D. The nerve electrode was implanted at the center of the sciatic nerve.

All lead wires were connected to a connection pin of an external device in order to collect continuous data, and the surface of the connected portion was sealed with dental cement (Vertex™ Self-Curing). Thereafter, noticeable signals of electroneurograms (ENGs) of the sciatic nerve against the mechanical stimulus were recorded at an interval of a week for 12 weeks by using a von Frey filament exhibiting a force of linear pressure corresponding to an amount of 75 g.

As a result, as illustrated in FIG. 18, the nerve electrodes in Examples 2 and 3 of the present invention were able to continuously record signals of electroneurograms even 12 weeks after the implantation, but in the case of the control electrode, no signals of electroneurograms were recorded. Further, with respect to the qualities of signals of electroneurograms when the nerve electrodes in Examples 2 and 3 were implanted, the signals exhibited the same result throughout the measurement period.

Meanwhile, nerves were stimulated through rat's soles using a mechanical stimulator. Electrical signals originated from the sciatic nerve are generally produced by activation of electroneurograms. Continuous signals of electroneurograms generated as a result of the mechanical stimulus were recorded through the implanted nerve electrode, and the recorded data was compared by using signal to noise ratio (SNRs) of the nerve electrode without any elimination of noise. The signal to noise ratio was exhibited by a heapmap produced by data recorded for 12 weeks, and is illustrated in FIG. 19.

In the result in FIG. 19, there was no big difference in signal to noise ratio between the nerve electrode in Example 2 and the nerve electrode in Example 3, and accordingly, it can be confirmed that the containing of the anti-fibrotic drug does not affect the quality of the signal to noise ratio. Meanwhile, Rat 6 into which the nerve electrode in Example 3 was implanted died of an unknown cause.

<Experimental Example 8> Histological Analysis of Site into which Nerve Electrode is Implanted After the nerve electrodes in the Examples of the present invention or the control electrode were or was each implanted into the sciatic nerve of the rat as in Experimental Example 7, rats were sacrificed by $CO_2$ in 2 weeks, 4 weeks, and 12 weeks after the implantation. The implanted nerve electrode and surrounding tissues were collected and fixed with 10% neutral-buffered formalin (BBC Biochemical, WA, USA). Thereafter, the sciatic nerve was treated by a general histological method.

Tissues were embedded in paraffin and sectioned into a thickness of 4 μm for hematoxylin-eosin (H&E, BBC Biochemical) and luxol fast blue-cresyl etch violet staining (LFB-CEV)(American MasterTech, California, USA).

The nerve area and the axonal indices (axonal density and total axon number) were measured by Leica Application Suite software (Leica Application Suite, Leica Microsystems, Wetzlar, Germany). The axonal density was calculated by dividing the average number of LFB-CEV positive myelinated axons in at least five sections by an area of the microscope photograph. The total myelinated axon number in the tissue was calculated by multiplying the nerve area and the axonal density.

As a result, as illustrated in FIG. 20, it can be confirmed that in the case of the nerve electrode in the Comparative Example, 4 weeks after the implantation, the cellular area is significantly decreased and the axonal density and the total axon number are also remarkably decreased while the cellular form is deformed. On the contrary, in the case of the nerve electrode in Example 2 of the present invention, until 12 weeks after the implantation, the cellular form was not significantly deformed, the change in cellular area is smaller than that of the nerve electrode in the Comparative Example, and the change in axonal density and total axon number was also slight. Furthermore, in the case of the nerve electrode in Example 3, which is a nerve electrode where tranilast was contained, the wetting phenomenon of fibrotic tissues was reduced, and the change in cellular area, axonal density, and total axon number was also the slightest.

Therefore, it can be seen that the nerve electrode of the present invention causes less axonal deformation than existing nerve electrodes, and as a result, edema, interneural inflammation, cellular infiltration, axonal atrophy, and the like are prevented. Further, it can be seen that the nerve electrode of the present invention can contain an anti-fibrotic drug without any change in performance, and as a result, the expression of fibrotic tissues may be reduced and the axonal structure may be maintained.

From the foregoing description, it will be understood by those skilled in the art to which the present invention pertains that the present invention can be embodied in other concrete forms without modifying the technical spirit or essential features of the present invention. In this regard, it should be understood that the above-described Examples are only exemplary in all aspects and are not restrictive. The scope of the present invention is represented by the claims to be described below rather than the detailed description, and it should be interpreted that the meaning and scope of the claims and all the changes or modified forms derived from the equivalent concepts thereto fall within the scope of the present invention.

INDUSTRIAL APPLICABILITY

According to the manufacturing method of the present invention, a nerve electrode which is excellent in porosity, permeability, flexibility, mechanical strength, and signal stability may be manufactured, and thus may be industrially usefully used.

In addition, in the nerve electrode manufactured according to the manufacturing method of the present invention, inflammation response, cellular infiltration, axonal atrophy, fibrosis of nerve cells, and the like also remarkably decreased, and thus may be usefully used in the nerve electrode field.

The invention claimed is:

1. A method of manufacturing a nerve electrode for sensing nerve signals, the method comprising the steps of: 1) manufacturing a poly (amic acid) fibrous sheet by electrospinning poly (amic acid), wherein the poly (amic acid) is synthesized by polycondensation of pyromellitic dianhydride (PMDA) and 4,4'-oxydianiline in N,N-dimethylacetamide, and the polycondensation of the PMDA and the 4,4'-oxydianiline in the N,N-dimethylacetamide is performed under a temperature equal to or less than 4° C. for more than one hour; 2) manufacturing a polyimide fibrous sheet by heat-treating the poly (amic acid) fibrous sheet at a temperature of 300° C. to 400° C.; 3) thermally compressing the polyimide fibrous sheet at a temperature of 80° C. to 140° C. under a pressure of 600,000 N/m$^2$ to 900,000 N/m$^2$ for 30 minutes to 6 hours; 4) inkjet printing a conductive ink on the polyimide fibrous sheet thermally compressed in Step 3); 5) heat-treating the polyimide fibrous sheet on which the conductive ink is inkjet printed in Step 4) at a temperature of 140° C. to 220° C.; and 6) applying poly(3,4-ethylene dioxythiophene)/poly (styrenesulfonate) (PEDOT/PSS) on the inkjet printed conductive ink by an electrochemical polymerization method, thereby enhancing the sensing of the nerve signals.

2. The method of claim 1, wherein the electrospinning in Step 1) is performed at a voltage of 10 kV to 40 kV.

3. The method of claim 1, wherein the heat treatment in Step 2) is performed for 30 minutes to 6 hours.

4. The method of claim 1, wherein the conductive ink in Step 4) comprises any one or more metal nanoparticles selected from the group consisting of a silver nanoparticle, a gold nanoparticle, a copper nanoparticle, an aluminum nanoparticle, a platinum nanoparticle, a titanium nanoparticle, an iridium nanoparticle, and an indium nanoparticle.

5. The method of claim 4, wherein the conductive ink comprises the silver nanoparticle.

6. The method of claim 1, wherein the heat treatment in Step 5) is performed for 30 minutes to 6 hours.

7. The method of claim 1, further comprising a step of containing an anti-fibrotic drug by bringing the nerve electrode into contact with a solution in which the anti-fibrotic drug is dissolved.

* * * * *